(12) United States Patent
Brugger et al.

(10) Patent No.: US 10,022,484 B2
(45) Date of Patent: Jul. 17, 2018

(54) FLUID CIRCUIT PRIMING METHODS, DEVICES, AND SYSTEMS

(71) Applicant: NXSTAGE MEDICAL, INC., Lawrence, MA (US)

(72) Inventors: James M. Brugger, Newburyport, MA (US); William J. Schnell, Libertyville, IL (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 334 days.

(21) Appl. No.: 14/765,001

(22) PCT Filed: Feb. 6, 2014

(86) PCT No.: PCT/US2014/015172
§ 371 (c)(1),
(2) Date: Jul. 31, 2015

(87) PCT Pub. No.: WO2014/124180
PCT Pub. Date: Aug. 14, 2014

(65) Prior Publication Data
US 2015/0367062 A1    Dec. 24, 2015

Related U.S. Application Data

(60) Provisional application No. 61/762,197, filed on Feb. 7, 2013, provisional application No. 61/761,405, filed on
(Continued)

(51) Int. Cl.
*A61M 1/36*    (2006.01)

(52) U.S. Cl.
CPC .......... *A61M 1/3646* (2014.02); *A61M 1/365* (2014.02); *A61M 1/3647* (2014.02); *A61M 1/3649* (2014.02)

(58) Field of Classification Search
None
See application file for complete search history.

(56) References Cited

U.S. PATENT DOCUMENTS

| 4,620,965 A | 11/1986 | Fukusawa et al. |
| 6,989,002 B2 | 1/2006 | Guala |

(Continued)

FOREIGN PATENT DOCUMENTS

| EP | 2397168 | 12/2011 |
| EP | 2462966 A1 | 6/2012 |

(Continued)

OTHER PUBLICATIONS

International Search Report and Written Opinion, dated Jul. 28, 2014, for International Application No. PCT/US14/15172.
(Continued)

*Primary Examiner* — Krishnan S Menon
*Assistant Examiner* — Ryan B Huang
(74) *Attorney, Agent, or Firm* — Potomac Law Group, PLLC; Mark Catan

(57) ABSTRACT

According to embodiments, priming systems, methods, and devices are disclosed which allow medical treatment devices which pump fluid to be primed with minimal operator intervention and a high level of convenience. A blood circuit with a filter fitted with one or more air vents on a non-blood compartment is attached to a treatment system and priming fluid pumped slowly through the blood circuit in a loop. The source of fluid may be elevated, or the pumping may generate pressure, such that priming fluid is forced through the membrane of the filter and out the air vent(s). In embodiments, the vents are hydrophobic which prevent fluid from being ejected, so the priming system can run without intervention.

20 Claims, 11 Drawing Sheets

Related U.S. Application Data on Feb. 6, 2013, provisional application No. 61/783,774, filed on Mar. 14, 2013, provisional application No. 61/926,704, filed on Jan. 13, 2014.

(56) References Cited

U.S. PATENT DOCUMENTS

| | | | |
|---|---|---|---|
| 7,901,579 B2 | 3/2011 | Brugger et al. | |
| 8,491,518 B2 | 7/2013 | Schnell et al. | |
| 8,496,613 B2 | 7/2013 | Zhou | |
| 8,834,403 B2 | 9/2014 | Kelly et al. | |
| 2002/0177786 A1 | 11/2002 | Balbo | |
| 2003/0010717 A1* | 1/2003 | Brugger | A61M 1/3643 210/650 |
| 2003/0010719 A1 | 1/2003 | Brugger et al. | |
| 2006/0091056 A1* | 5/2006 | Brugger | A61M 1/3627 210/321.88 |
| 2009/0008306 A1 | 1/2009 | Cicchello et al. | |
| 2009/0076433 A1* | 3/2009 | Folden | A61M 1/3643 604/4.01 |
| 2009/0101576 A1* | 4/2009 | Rohde | A61M 1/3643 210/646 |
| 2009/0312686 A1 | 12/2009 | Sakamoto et al. | |
| 2010/0063445 A1 | 3/2010 | Sternberg et al. | |
| 2011/0213289 A1 | 9/2011 | Toyoda et al. | |
| 2013/0025357 A1 | 1/2013 | Noack et al. | |
| 2013/0098838 A1 | 4/2013 | Beden et al. | |

FOREIGN PATENT DOCUMENTS

| | | |
|---|---|---|
| JP | 2009-165500 | 7/2009 |
| JP | 2012-095843 | 5/2012 |
| WO | 2005089832 A2 | 9/2005 |
| WO | WO 2007/072771 | 6/2007 |
| WO | WO 2011/099521 | 8/2011 |
| WO | WO 2012/150679 | 11/2012 |
| WO | WO 2013/183599 | 12/2013 |
| WO | WO 2014/050468 | 4/2014 |
| WO | WO 2015/068833 | 5/2015 |

OTHER PUBLICATIONS

Extended European Search Report and Written Opinion for European Patent Application No. 147492011 dated Mar. 1, 2017.
Supplementary Partial European Search Report for European Application No. 14749201.1 dated Nov. 21, 2016.

* cited by examiner

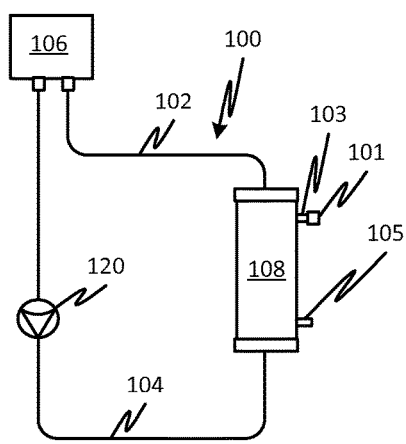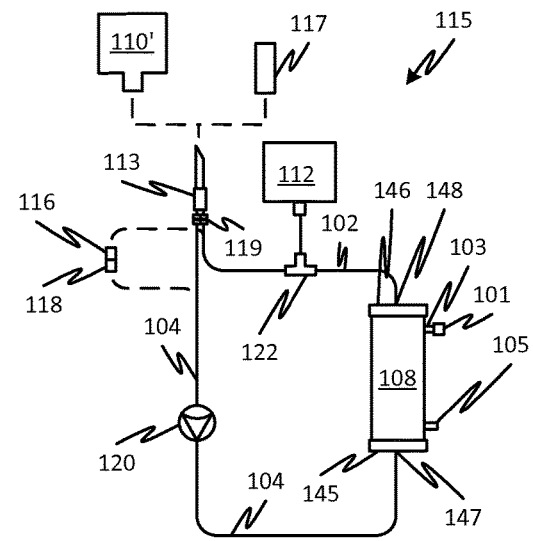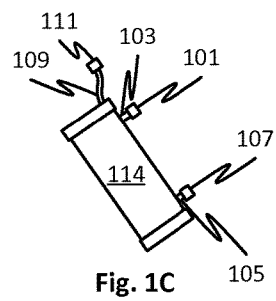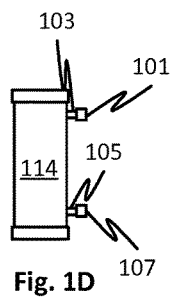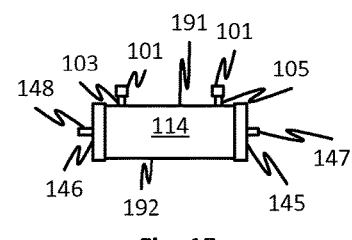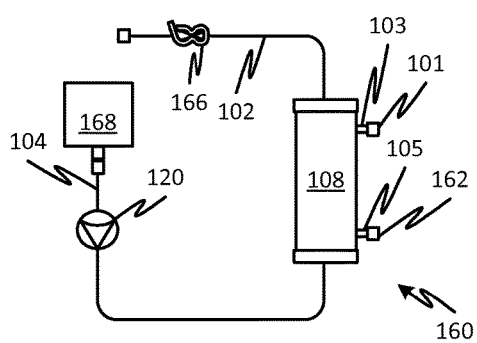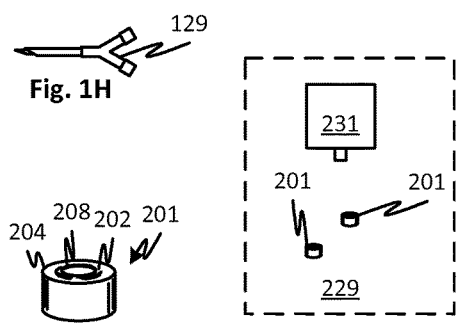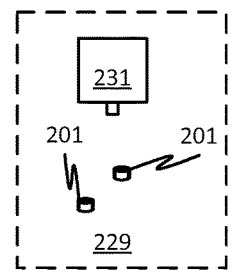

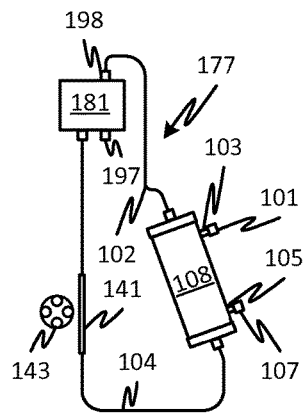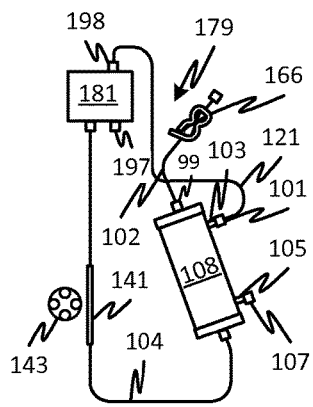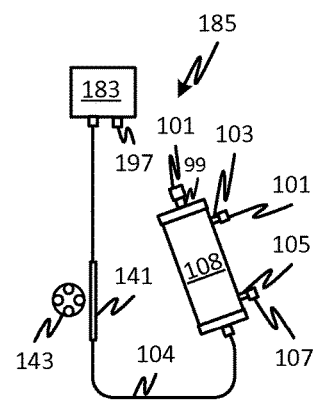
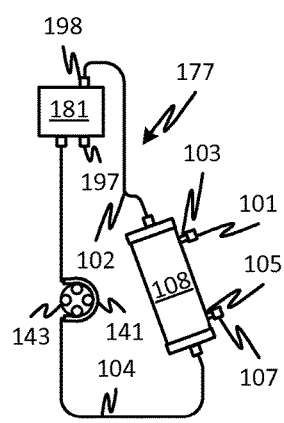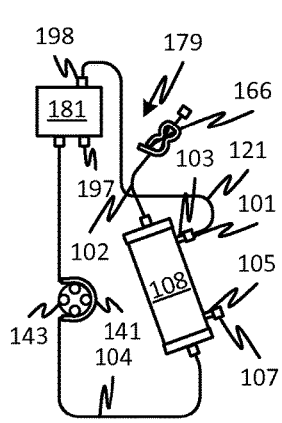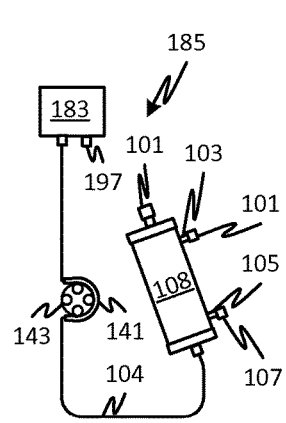
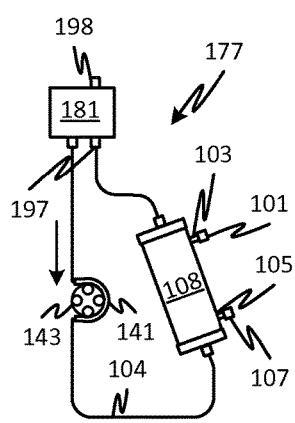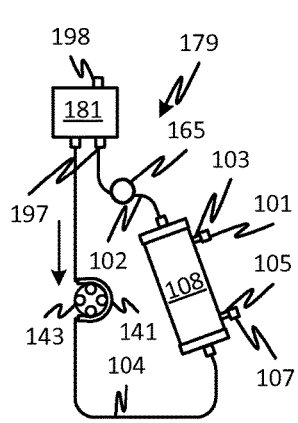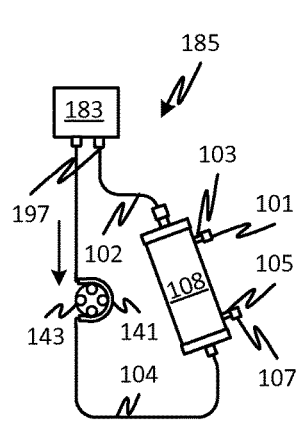

FLUID CIRCUIT PRIMING METHODS, DEVICES, AND SYSTEMS

FIELD

The presently disclosed subject matter relates generally to medical treatment methods, devices, and systems. More specifically, in embodiments at least, the presently disclosed subject matter relates to medical treatment methods, device, and systems for the treatment of renal failure.

BACKGROUND

Many blood treatment systems employ filters to allow for diffusion or convective exchange of fluid and/or molecular species to and from blood. In dialysis, for example, diffusion exchange is provided in order to remove waste products from the blood of a person. Hemofiltration is similar but relies primarily on convection of fluids including waste materials combined with convective replacement of the removed fluid. Other treatments provide combinations of diffusion and convective transport and the varying relative contributions of convective and diffusive transport.

Dialyzers and hemofilters that are in common use are essentially the same and sometimes structurally identical. The most common construction is a disposable device with a microtubular filter fiber bundle that is terminated by inlet and outlet headers to provide inlet and outlet flow to and from the blood compartment of the filter. A casing surrounds the bundle and defines a non-blood (e.g., waste or medicament such as dialysate) compartment for a non-blood fluid to collect or flow. At least one port is in fluid communication with this non-blood chamber or channel (the term "non-blood compartment" may be used to identify broadly a compartment, chamber, or channel or any other circuit portion based on its being on the non-blood compartment of the membrane, the general term being "compartment"). Other types of hemofilters and dialyzers are referred to generally as filters, and there are configurations other than microtubular fiber bundle types that exist as well.

Extracorporeal blood treatment is commonly performed in a clinical setting with professional and highly trained caregivers and system operators. Some systems are operable by lower skilled personnel including at-home dialysis patients who may rely on a helper. In some known blood treatment systems, a blood circuit is formed by connecting a filter, a venous line and an arterial line in series. The circuit may be primed by circulating a priming fluid on the blood compartment to fill the blood compartment of the circuit. In flowing the fluid through the blood compartment, a closed loop may be formed. After the blood compartment is primed, the non-blood compartment may be filled with fluid by attaching a source of fluid, which may be dialysate and pumping the fluid through the non-blood compartment of the filter. Filters may trap air, especially because they tend to be constructed with a high surface area compactly arranged in a small volume. Operators routinely manipulate the filter to cajole air into flowing out of the filter. The manipulations may include tilting the filter and tapping on it as well as controlling the flow in a way that helps the air to accumulate and flow out of the filter.

The process of priming takes time and attention from workers. It also adds tedium and distraction to the task of delivering care. It poses risks if not consistently performed or if a worker has been improperly trained and can make treatment less efficient if not properly done. Thus, it is desirable to provide methods, devices, and systems that allow for priming that is convenient and effective.

SUMMARY

According to embodiments, priming systems, methods, and devices are disclosed which allow medical treatment devices that pump fluid to be primed with minimal operator intervention and/or with a high level of effectiveness for air removal, particularly from the membrane itself. In embodiments, a blood circuit has a filter which is fitted with one or more air vents of a non-blood compartment. The filter is attached to a treatment system and priming fluid pumped into and through the blood circuit. In embodiments, the priming fluid may flow in a loop. The source of fluid may be elevated, or the pumping may generate pressure, such that priming fluid is forced through the membrane of the filter. In embodiments, the air in the non-blood compartment flows out the one or more air vent(s). In embodiments, the vents are hydrophobic, which prevents fluid from being ejected, so that the priming system can run without intervention. In embodiments, the filter is positioned substantially vertically with priming fluid flowing from the bottom up. In embodiments, the filter is positioned in the normal treatment position. In embodiments, the filter is not tilted, inverted, tapped, or shaken and priming fluid thoroughly wets the membrane from the blood compartment through to the non-blood compartment without applying any fluid to the non-blood compartment so that the membrane is dry on the non-blood compartment side thereof until wetted by flow of priming fluid through the membrane from the blood compartment side. In further embodiments, the filter casing is evacuated to a very low pressure (less than 0.1 bar) and priming fluid is flowed into the filter from either side of the membrane such that air cannot be trapped in the membrane. In embodiments, priming is effective to provide substantially 100% of a filter's dialytic clearance potential (KtV/A=clearance per unit membrane area) as a result of the membrane being effectively free of air.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 1A shows a priming set-up for a blood circuit of an extracorporeal blood treatment system, according to embodiments of the disclosed subject matter.

FIG. 1B shows a priming set-up for a blood circuit of an extracorporeal blood treatment system, according to embodiments of the disclosed subject matter.

FIG. 1C shows, in a first orientation, a blood treatment device, for example a dialyzer, with one or more air vents, according to embodiments of the disclosed subject matter.

FIG. 1D shows, in a second orientation, a blood treatment device, for example a dialyzer, with one or more air vents, according to embodiments of the disclosed subject matter.

FIG. 1E shows, in a third orientation, a blood treatment device, for example a dialyzer, with one or more air vents, according to embodiments of the disclosed subject matter.

FIG. 1H shows a dual lumen patient access which may be used advantageously with priming methods devices and systems, according to embodiments of the disclosed subject matter.

FIGS. 1Q, 1T and 1W shows a priming configuration in which priming fluid flows into a filter membrane by gravitation, according to embodiments of the disclosed subject matter.

FIGS. 1R, 1U, and 1W show another priming configuration in which priming fluid flows into a filter membrane by gravitation, according to embodiments of the disclosed subject matter.

FIGS. 1S, 1V, and 1Y show yet another priming configuration in which priming fluid flows into a filter membrane by gravitation, according to embodiments of the disclosed subject matter.

FIG. 1X is a priming configuration in which priming fluid flows in a reverse direction relative to the treatment direction so that it flows from the top of the microtubular fiber membranes downwardly, which also illustrates the use of a flow restrictor to ensure the transmembrane pressure does not become large enough to permit priming fluid to flow from a high portion of the membrane to a low portion on the non-blood compartment side, according to embodiments of the disclosed subject matter.

FIG. 2A shows a vented port cap for use on blood treatment devices, according to embodiments of the disclosed subject matter.

FIG. 2B shows a kit with a vented port cap and a container of priming fluid, according to embodiments of the disclosed subject matter.

FIG. 2C shows a priming setup for a blood circuit of an extracorporeal blood treatment system, according to embodiments of the disclosed subject matter.

DETAILED DESCRIPTION

Figure 1F:
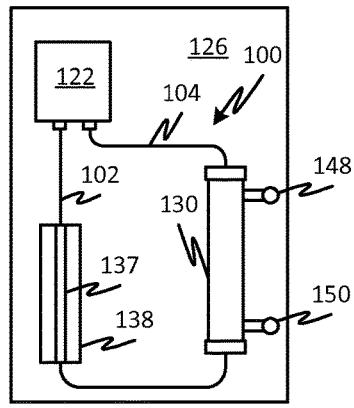
FIG. 1F shows a fluid circuit including a cartridge with a blood treatment device, for example a dialyzer, with one or more air vents, according to embodiments of the disclosed subject matter.

FIG. 1A shows a fluid circuit 100 having venous 102 and arterial 104 lines connected to a blood compartment (not shown directly) of a filter 108 thereby forming a flow loop with the filter 108 and a container 106. The filter 108 may be a dialyzer of the type described in the Background section having a microtubular fiber bundle with lumens of the microtubular fibers, which are connected by inlet and outlet headers, forming the blood compartment of the filter 108. A pump 120 pumps fluid through the fluid circuit 100. During a priming operation, the venous 102 and arterial 104 lines are connected to a source of priming fluid, which may be container 106. That is, priming fluid may be provided in the container 106 which, upon connection to the venous 102 and arterial 104 lines, provides priming fluid to the arterial line and forms a loop with the filter. Priming fluid, for example sterile saline, flows from the container 106 into the arterial line 104 pumped by the pump into the filter 108 through a blood compartment thereof. The fluid exits the blood compartment of the filter 108 and passes through the venous line 102 back into the container 106. The fluid collects in the container 106 and may recirculate. Air bubbles may collect and settle in container 106 thereby removing air from the circulating flow. Thus, the container 106 may serve the multiple purposes of an air removal device (with air settling out of the flow therein), a flow loop completion element, and a source of priming fluid. In embodiments, the container 106 is a flexible-bag-type of container.

Filter 108 has two ports 103 and 105 which may be used for flowing dialysate across the non-blood compartment of the filter membrane. One of the ports 103 has a vented cap 101. The vented cap 101 may be configured to fit a predefined port of a predefined filter and allow air to passively flow through it, for example from the non-blood compartment, while blocking water or aqueous fluid from passing through it. An example of a vented cap 101 is a plastic snap or screw-fitting cap with a hydrophobic sterile barrier membrane fitted in an axial center face thereof. The sterile barrier may include a membrane whose pores are 0.3 micron or smaller so as to prevent passage of pathogens. The vented cap 101 permits fluid from the blood compartment to pass through it and displace the air until air is removed from the non-blood compartment. In operation, a positive pressure may be developed by the pumping such that the blood compartment has a higher pressure than the non-blood compartment. Vented cap 101 may be replaced by other devices that provide the function of allowing gas to pass through it while blocking passage of aqueous fluids. This function may be provided through an active or passive mechanism such as a control valve (manual or automated), float valve, non-sterile-barrier membrane, etc.

The positive transmembrane pressure (TMP) across the filter membrane allows fluid to flow through the membrane thereby removing air in a single direction. At the time of priming, the filter is dry and no fluids are provided to the dialysate compartment until the membrane is sufficiently (preferably entirely) wetted by the flow through the membrane from the blood compartment to the non-blood compartment. The flowing of priming fluid along the blood compartment at a positive pressure relative to the non-blood compartment and progressively in a single direction from a lower end of each fiber upwardly while maintain a condition where no fluid wets the outside of the fibers, or more generally, the non-blood compartment-side of the membranes, until they are wetted from the blood compartment-side, the air is effectively pushed out of the membrane in a manner such that no bubbles are formed. If the non-blood side of the membranes are wetted before the priming fluid has progressed completely across the thickness of the membrane, air may become trapped within the tiny channels, thus requiring excessive pressure and/or time for the transmembrane pressure to force the trapped bubble(s) through the tiny membrane channel.

Although filter 108 is shown in a vertical orientation, filter 108 can be oriented in other ways such that the port 103, with the vented cap 101, is at the top of the filter 108. Note also, as mentioned above, the port through which air is vented does not need to be one used to flow fluid into or out of filter 108 through or from the non-blood compartment. By positioning the filter with the vented port at a high location, this minimizes the amount of air that can be trapped above the port and within the non-blood compartment. The orientation may play another role by which it helps ensure that fluid progresses solely from the blood compartment, across the membrane, to the non-blood compartment by ensuring that priming fluid does not contact the non-blood compartment side of the membrane before the membrane is fully wetted from the blood compartment side thereof. The possible roles of orientation with regard to this concern is discussed with reference to FIGS. 1J and 1K, below.

FIGS. 1C, 1D, and 1E show different orientations of the filter that position at least one of the ports (103 or 105) at the highest position of the filter 114. Referring to FIG. 1C, a filter 114 may be of conventional construction. In this example, an air relief channel 109 may have a vented cap or sealed cap 111 which may allow air to be pass through it from a blood compartment header of the filter 114 during treatment or at other times. FIG. 1C also illustrates the use of two vented caps 101 and 107 on respective ports 103 and 105. Although one of the ports 105 is not at a position where it is at the top, some air may be removed from it thereby speeding the priming process. FIG. 1D shows a vertical orientation and again, the orientation is such that the port 103 is at the top. Note that in positioning the port at the top, the axial and radial position of the port are relevant. Thus, in FIG. 1E, the port 103 and port 105 are at the top because the radial line (radial with respect to the longitudinal axis) coinciding with the port is directed upwardly. The filter 114 may be in a variety of different orientations while achieving the air removal effect described. Other types of filters may require different orientations in order to maximize their ability to remove air. The orientations shows in FIGS. 1C, 1D, and 1E may not all equally minimize the risk of wetting the non-blood compartment-side of the membrane or minimize the risk of trapping air in the non-blood side of the membrane. At least the shape of the filter, the flow resistance of the priming fluid within the microtubular fibers (or other type of filter membrane structure), the transmembrane pressure at all points of the membrane, and the flow rate may be relevant to ensuring these risks are minimized.

FIG. 1B shows a fluid circuit 115, which has the same basic function of fluid circuit 100 of FIG. 1A, including, for example, the same filter 108, pump 120, and venous 102 and arterial 104 lines and identified variants thereof. FIG. 1B illustrates a dual lumen spike 113 that may be used to make the two connections simultaneously to a container 110' of priming fluid that were discussed relative to container 106 above. The dual lumen spike 113 may be provided as part of a fluid circuit having the venous 102 and arterial 104 lines pre-connected and a cap 117 to seal the dual lumen spike 113 from the environment and protected against contamination. The dual lumen spike has two fluid connections that allow a flow into and out of a container without recirculation. The recirculation is inhibited provided that the openings in the dual lumen spike are remote from each other.

The dual lumen spike 113 may be connected to the venous 102 and arterial 104 lines by releasable connectors 119. Once released, the connectors 119 of the venous 102 and arterial 104 lines may be connected to a patient access device 129 (FIG. 1H) to perform a treatment. The connection of the dual lumen spike 113 to the container 110' is effective to form a flow loop that includes the venous 102 and arterial 104 lines and the filter. Fluid may be circulated in the loop to remove air by permitting it to settle out of the priming fluid into the container 110' and by removing air from the filter 108 through the vented cap 101 as described above.

FIG. 1B also illustrates alternative embodiments in which priming fluid container 112 is connected at a junction 122 for example a needleless connector to either the venous 102 or arterial 104 line. In this case, connectors 116 and 118 for connecting to a patient access device, for example a dual lumen needle 129 (See FIG. 1H), can be connected together to form a flow loop. After priming, the container 112 can be disconnected or clamped off. The patient access device, e.g., 129 of FIG. 1H, can then be connected to the connectors 116 and 118 for treatment.

Referring to FIG. 1F, a cartridge 126 has a fluid circuit with venous 102 and arterial 104 lines, a filter 130, and a pump tubing segment 137. The cartridge 126 has a cutout 137 or is otherwise arranged to permit a treatment machine to engage the pump tubing segment 137. Connectors 148 and 150 connect to a dialysate balancing system of a treatment machine configured, for example as the machine described below with reference to FIG. 1G. Any treatment machine is contemplated that circulates fluid between the connectors 148 and 150 through the filter, or which draws fluid from one of the connectors 148 in the configuration where there is only one as would be for a hemofilter, for example. The cartridge 126 may provide support for the filter 130 such that it is automatically oriented in a desired way to place one of the connectors 148 at a top position. In this way, the provision of a vent at the connector 148 may allow the removal of air from the vent. In general the filter 130 may be oriented and positioned so as to help to ensure that no excess, or at least a limited excess, of priming fluid may accumulate on a membrane non-blood second side at any points of the membrane non-blood side so that any such excess cannot flow far or, at least, cannot run to a portion of said non-blood side which may not have been fully wetted from a blood side of the membrane as a result of priming fluid traversing the membrane from the blood side. As in the above-discussed embodiments, the connectors 148 and 150 may be fitted with a vented cap 101 which may be removed, after priming, to make a connection to the non-blood fluid management system, for example the dialysate-circulating portions of a treatment machine. A priming fluid container 122 may be connected to the venous 102 and arterial 104 lines for priming and can be replaced by a patient access as described. The priming fluid container 122 may be formed in, or attached to, the cartridge 126 and delivered as a unit along with the fluid circuit 100. The filer 130 may be integrated in the cartridge 126 as a deliverable consumable or may be attached to fitments provided on the cartridge 126, according to respective embodiments.

Figure 1G:
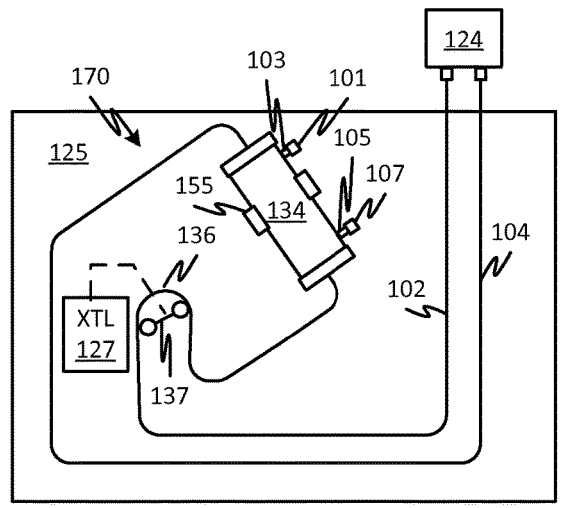
FIG. 1G shows a blood treatment system for purposes of illustrating apparatus and methods for using a priming configuration adapted for new devices and legacy blood treatment machines, according to embodiments of the disclosed subject matter.

FIG. 1G shows a blood treatment machine 125 with a support 155 configured to hold the filter 134 in a predefined orientation that provides for the port 103 to be in the top position relative to the filter 134. In alternative embodiments, the support 155 is configured to hold the filter 134 in a position that helps to ensure that no excess, or a limited excess, of priming fluid may accumulate on a membrane non-blood second side at any points of the membrane non-blood side so that any such excess cannot flow far or, at least, cannot run to a portion of said non-blood side which may not have been fully wetted from a blood side of the membrane as a result of priming fluid traversing the membrane from the blood side. A blood circuit 170 (a type of fluid circuit) is connected to the blood treatment machine for priming the blood circuit. A vented cap 101 and 107 may be provided on each of the two ports 103 and 105. The machine 125 may be configured as many treatment machines are, with a controller 127 that controls a speed of pump 137 such that fluid is driven through the venous 102 and arterial 104 lines and the filter 134 at a selectable speed and also stopped to halt flow. The venous 102 or arterial 104 line may be fitted with a pump tubing segment 136 that engages a peristaltic pump rotor of the pump 137. A priming fluid container 124 provides priming fluid to the blood circuit 170. During priming, the vented cap 101 or vented caps 101 and 107 allow air to be removed from the blood circuit 170 while the pump 137 circulates the priming fluid through the blood circuit 170 and the container 124, simultaneously removing air through the vent(s) 101 and/or 107. The controller 127 may include a user interface or other control I/O device that allows the speed of the pump and/or on/off state of the pump 137 to be selected. Such a control I/O may be provided for any of the pumps identified.

FIG. 2C illustrates a fluid circuit 160 embodiment that is similar to that of FIG. 1A, except that instead of pumping fluid in a loop formed by the venous 102 and arterial 104 lines and the container 106, the pump 120 is used to pump priming fluid from a container 168 that holds priming fluid (or, alternatively, fluid may be pumped from any other source, such as an inline source provided at a clinic) into the filter 108. Here one of the non-blood compartment ports 105 is capped by a sealing cap 162 to seal it and the other port has a vented cap 101. Both of non-blood compartment ports 103 and 105 may be vented, in alternative embodiments. The pump 120 may be operated at a rate that is lower than a rate used for blood treatment. As priming fluid is forced into the blood compartment of the filter 108, the fluid fills the blood compartment and pushes its way into the membrane and out into the non-blood compartment with air venting from the vented cap 101. A user may set up the fluid circuit 160 as illustrated with a clamp 166 closed on the arterial line 102 and allow the pump to operate until the non-blood compartment is completely filled. The filter 108 may be tilted to place the port 103 with vented cap 101 at a higher point so that very little air volume remains thereabove such that as fluid fills the non-blood compartment, all, or nearly all, of the air is vented. Here, as in any of the embodiments, a filter 750 as described below with reference to FIG. 13 may be used, as may any filter with a built in hydrophobic vent on a non-blood compartment of the filter. In any of the embodiments, the vent may be replaced with a closeable valve or a clampable line or any other suitable means for permitting air to flow out of the non-blood compartment such that priming fluid can flow into the blood compartment and through the membrane.

Figure 1J:
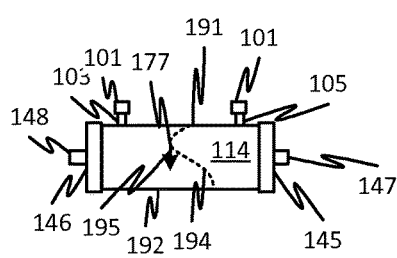
FIGS. 1J and 1K illustrate profiles suggesting how the advancement of fluid through the blood compartment of a filter may have features that permit unfavorable priming and favorable priming, respectively.
Figure 1K:
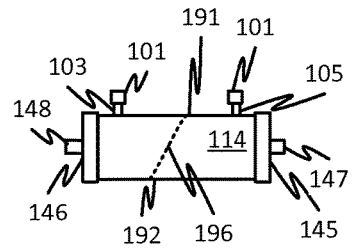
Figure 1L:
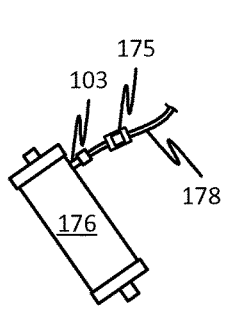
FIG. 1L shows a filter with a vented line stemming from a non-blood compartment port, according to embodiments of the disclosed subject matter.

Referring to FIG. 1L, the venting of the non-blood compartment can be provided for by using a vented line 178 connected to a non-blood compartment port 103 of a filter 176, such as a dialyzer type filter. A vent 175 may be connected, or integrated in, a non-blood line 178 as part of a treatment fluid circuit set. The vent 175 may be, for example, as described in U.S. Pat. No. 6,989,002, which is hereby incorporated by reference herein in its entirety. Alternatively, air removal chambers, drip chambers, and other types of air removal devices may be used. This is the case for any of the disclosed embodiments. That is, the gas removal devices may be of any form to permit a transmembrane pressure to facilitate the movement of priming fluid across the membrane to wet it. Note that in any of the embodiments, gas does not need to be vented to the outside, for example, a container capable of holding any of the gas or air removed from the filter may be employed.

Figure 1M:
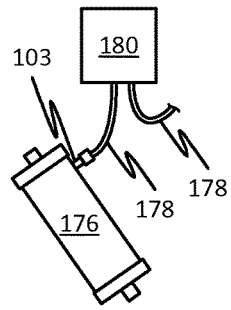
FIG. 1M shows a filter with an enclosed gas-relief line stemming from a non-blood compartment port, according to embodiments of the disclosed subject matter.

FIG. 1M shows a filter with an enclosed gas-relief line 178 (which may form part of a non-blood portion of a treatment fluid circuit) stemming from a non-blood compartment port, according to embodiments of the disclosed subject matter. Such a container may be removed once priming is complete. Such a container 180, as shown in FIG. 1M, may be positioned in the line 178 on the non-blood side of the circuit as was vent 175.

Figure 1N:
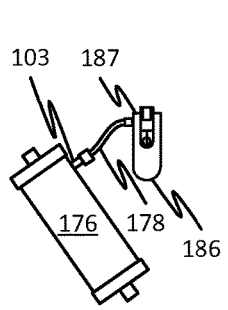
FIG. 1N shows an embodiment in which a chamber with a float vent valve 187 is employed to provide for the venting of gas, according to embodiments of the disclosed subject matter.

FIG. 1N shows an embodiment in which a chamber 186 with a float vent valve 187 is employed to provide for the venting of gas. The float vent valve 186 is shown attached to a line 178, but could also be integrated in the filter 176 in alternative embodiments, or detachably affixed directly to the filter and removed after priming to serve the same function.

Figure 1P:
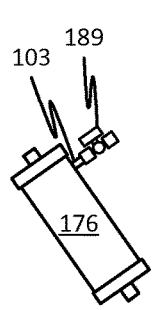
FIG. 1P shows a manually operable valve which may be controlled by an operator during priming to vent gas from the non-blood compartment, according to embodiments of the disclosed subject matter.

FIG. 1P shows a manually operable valve 189 which may be controlled by an operator during priming to vent gas from the non-blood compartment as it accumulates. The valve 189 may be operated to open it when gas has accumulated in the non-blood compartment and closed when the liquid level reaches the valve 189 or gets close to it. This may be done until the membrane is fully wetted.

FIG. 1Q shows a priming configuration in which priming fluid flows into a filter membrane by gravitation and without pumping, according to embodiments of the disclosed subject matter. The container 181 is connected to the venous 102 and arterial 104 lines of a blood circuit 177 forming a loop. The venous line 102 is connected to the top connector 198 of the container 181. The filter 108 non-blood compartment ports 103 and 105 may be capped with venting caps 101, 107 or the lower port 105 may be capped to seal it and the upper port 103 may be capped with a vented cap. In embodiments, the container 181 as supplied is filled with priming fluid and may also be preconnected to the filter 108 with a kink type closure or frangible closure or any other suitable device to isolate the fluid until priming is to be done. The container 181, filled with priming fluid, is raised to an elevation such that it is above the top of the filter 108. This causes fluid to flow by gravity into the filter and as well by gravity back up toward the container at least to a point where it reaches the fluid level within the container or the arterial line. The force of the fluid column creates a pressure gradient that forces fluid through the membrane and through the microtubular fiber lumens. Since the transmembrane pressure is a result of the fluid column height, fluid is forced through the lower parts of the microtubular fiber lumens at a higher rate than at the higher portions, the force and rate changing progressively with height. This minimizes the chance that fluid will weep entirely through the membrane at high position and prematurely wet lower portions of the microtubular fiber external surfaces before such lower portions are wetted by fluid traversing through the membrane. In this way the risk of trapping air within the membrane is minimized.

Once the fluid has wetted the membrane, which can be determined as mentioned above, by an operator based on a predefined time employing a predefined height of the container 181 with respect to the filter 108 and any other relevant factors, the venous line 102 can be disconnected (at connector 198) and lowered to a level that brings the priming fluid up to the end of it, whereupon it can be connected to the container 181 such that both arterial 104 and venous 102 lines are filled. Referring to FIG. 1T, alternatively, before disconnecting the venous line 102 a pump tube segment 141, may be installed on a peristaltic pump actuator 143 to pinch off the pump segment and thereby prevent any backward flow (venous end to arterial end of filter 108) of the priming fluid. Referring to FIG. 1W, the connector 198 can then be connected to a lower connector 197 of the container 181. Then the pump can be run in the forward treatment direction (arterial line 104 to filter 108 to venous line 102 to circulate priming fluid through the filter 108 and the container capturing any gas in the container 181. The circulation can be very brief since there is only a need to flow the residual air in the venous line 102 above the fluid level in the container to clear the loop of gas. The rate of this pumping can be very slow to ensure no turbulence-generated bubbles are ingested in the arterial line 104. Once the pumping is completed, fluid can be pumped through the non-blood compartment of the filter 108 and further preparation for treatment made.

In an alternative embodiment, the venous line 102 can be capped with a vent or valve or some other gas relief device and the end thereof held at a position above the fluid level in the container 181, for example, by taping it to the container 181. In this case, a vent can be a non-hydrophobic vent because the fluid level would not rise to the level required.

FIG. 1R shows a priming configuration in which priming fluid flows into a filter membrane by gravitation, without pumping, according to embodiments of the disclosed subject matter. The container 181 is connected to the arterial line 104 of a blood circuit 179. A priming return line 121 connects the port 103 of the non-blood side to a top connector 198 of the container 181. In embodiments, the container 181 as supplied is filled with priming fluid and may also be preconnected to the filter 118 with a kink type closure or frangible closure or any other suitable device to isolate the fluid until priming is to be done. The container 181, filled with priming fluid, is raised to an elevation such that it is above the top of the filter 108. The venous line 102 may be clamped or a cap placed on the venous blood port 99 to seal it. Fluid flows by gravity into the filter and is forced by the fluid column pressure through the membrane into the non-blood compartment where gas is vented through the vented cap 101. At the same time gas flows out through the priming return line 121 and ultimately priming fluid flows into the priming return line 121. If enough fluid remains in the container 181, priming fluid will flow through the top connector 198 into the container. Here again, the force of the fluid column creates a pressure gradient that forces fluid through the membrane and through the microtubular fiber lumens. Since the transmembrane pressure is a result of the fluid column height, fluid is forced through the lower parts of the microtubular fiber lumens at a higher rate than the at higher portions, the force and rate changing progressively with height. This minimizes the chance that fluid will weep entirely through the membrane at higher position and prematurely wet lower portions of the microtubular fiber external surfaces before such lower portions are wetted by fluid traversing through the membrane. In this way the risk of trapping air within the membrane is minimized.

Once the fluid has wetted the membrane, which can be determined as described above or by inspection by an operator, the priming return line 121 can be removed and the port 103 capped or connected to a dialysate line. The venous line 102 can be unclamped to allow fluid to flow into it until it reaches the end thereof, whereupon it can be connected to the container 181 such that both arterial 104 and venous 102 lines are filled. Referring to FIG. 1U, alternatively, before unclamping the venous line 102 a pump tube segment 141, may be installed on a peristaltic pump actuator 143 to pinch off the pump segment and thereby prevent any backward flow (venous end to arterial end of filter 108) of the priming fluid. Referring to FIG. 1W, the connector 198 can then be connected to a lower connector 197 of the container 181. Then the pump can be run in the forward treatment direction (arterial line 104 to filter 108 to venous line 102) to circulate priming fluid through the filter 108 and the container capturing any gas in the container 183. Once the circulation is completed, which can be very brief since there is only a need to flow the residual air in the venous line 102 above the fluid level in the container to clear the loop of air. The rate of this pumping can be very slow to ensure no turbulence-generated bubbles are ingested in the arterial line 104. Once the pumping is completed, fluid can be pumped through the non-blood compartment of the filter 108 and further preparation for treatment can be made.

FIG. 1S shows a priming configuration in which priming fluid flows into a filter membrane by gravitation and without pumping, according to embodiments of the disclosed subject matter. The container 183 is connected to line 104 of a blood circuit 185. The filter 108 non-blood compartment ports 103 and 105 may be capped with venting caps 101, 107 or the lower port 105 may be capped to seal it and the upper port 103 may be capped with a vented cap. The blood compartment venous port 99 is capped, e.g., with another venting cap 101. In embodiments, the container 183 as supplied is filled with priming fluid and may also be preconnected to the filter 108 with a kink type closure or frangible closure or any other suitable device to isolate the fluid until priming is to be done. The container 183, filled with priming fluid, is raised to an elevation such that it is above the top of the filter 108. This causes fluid to flow by gravity into the filter and as well by gravity back up toward the container at least to a point where it reaches the fluid level within the container or the arterial line. The force of the fluid column creates a pressure gradient that forces fluid through the membrane and through the microtubular fiber lumens such that gas can vent from both the blood compartment and the non-blood compartment through the venting caps 101. Since the transmembrane pressure is a result of the fluid column height, fluid is forced through the lower parts of the microtubular fiber lumens at a higher rate than at the higher portions, the force and rate changing progressively with height. This minimizes the chance that fluid will weep entirely through the membrane at higher positions and prematurely wet lower portions of the microtubular fiber external surfaces before such lower portions are wetted by fluid traversing through the membrane. In this way the risk of trapping air within the membrane is minimized.

Once the fluid has wetted the membrane, which can be determined as mentioned above, by an operator based on a predefined time employing a predefined height of the container 183 with respect to the filter 108 and any other relevant factors, the vent caps 101 can be removed from, and a venous line 102 can be connected to, blood compartment port 99 while the distal (patient access) end of the venous line 102 is lowered to a level that brings the priming fluid up to the end of it, whereupon it can be connected to the container 181 at port 197 such that both arterial 104 and venous 102 lines are filled and a loop is formed. Referring to FIG. 1V, alternatively, before disconnecting the venous line 102, a pump tube segment 141 may be installed on a peristaltic pump actuator 143 to pinch off the pump segment and thereby prevent any backward flow (venous end to arterial end of filter 108) of the priming fluid. Referring to FIG. 1Y, the vent cap 101 can be removed from, and a venous line 102 can be connected to, blood compartment port 99 while the distal (patient access) end of the venous line 102 may be connected to the container 183 at port 197 to form a loop. The pump can then be run in the forward treatment direction (arterial line 104 to filter 108 to venous line 102) to circulate priming fluid through the filter 108 and the container capturing any gas in the container 183. The circulation can be very brief since there is only a need to flow the residual air in the venous line 102 above the fluid level in the container to clear the loop of gas. The rate of this pumping can be very slow to ensure no turbulence-generated bubbles are ingested in the arterial line 104. Once the pumping is completed, fluid can be pumped through the non-blood compartment of the filter 108 and further preparation for treatment can be made.

FIG. 1X is a priming configuration in which priming fluid flows in a reverse direction relative to the treatment direction so that it flows from the top of the microtubular fiber membranes downwardly, which also illustrates the use of a flow restrictor to ensure the transmembrane pressure does not become large enough to permit priming fluid to flow from a higher portion of the membrane to a lower portion on the non-blood compartment side, according to embodiments of the disclosed subject matter. If the transmembrane pressure is high enough, premature dry-side wetting can occur, that is, fluid can weep through to the non-blood compartment side and run down along the surface thereby wetting a previously dry portion of the non-blood compartment side of the membrane and potentially causing a bubble to be trapped. In the configuration of FIG. 1X, the pump actuator is driven in reverse such that priming fluid flows from the top down through the filter. The risk of premature dry-side wetting can be minimized or eradicated by controlling the transmembrane pressure by means of a regulation device 165. For example, regulation device 165 may include a flow restrictor that, in conjunction with a controller and the speed of the actuator 143, causes the transmembrane pressure to be maintained at a level that has previously been determined for the type of filter membrane to prevent premature dry-side wetting. In membranes that are highly hydrophilic, for example, it may be necessary to maintain a negative transmembrane pressure such that capillary action causes the membrane to be fully wetted. A negative pressure can easily be established by means of a controller and may advantageously employ a pressure sensor and active regulation device (for example one that varies the amount of flow restriction) using negative feedback control to maintain a predefined pressure. The pressure sensor in such a device may be positioned between the regulation device 165 and the filter 108.

Note in any of the embodiments, sensors and/or controls as well as interfaces for output and input by a user may be used to provide the functions described.

Note that in any of the embodiments, it may unnecessary, depending on the type of membrane, for a positive transmembrane pressure (blood to non-blood compartment-side) to be developed by a pump. In fact, the wetting of the membrane may be developed in the absence of a transmembrane pressure which is higher on the blood compartment side than on the non-blood compartment side. In an example embodiment, the priming fluid is pumped in such a manner that a negative transmembrane pressure (lower on the blood compartment side) is developed, for example where the blood circuit pump draws fluid through the filter. In such an embodiment, the capillary forces may be sufficient to ensure priming fluid traverses the membrane and gravity may still ensure that the lower portions of the membrane are at a higher transmembrane pressure than upper portions such that no excess, or a limited excess, of priming fluid may accumulate on a membrane non-blood second side at any points of the membrane non-blood side so that any such excess cannot flow far or, at least, cannot run to a portion of said non-blood side which may not have been fully wetted from a blood side of the membrane as a result of priming fluid traversing the membrane from the blood side.

Note that in any of the embodiments, although discussed in terms of a blood compartment and a non-blood compartment, the principles may applied to other kinds of devices, such as ones in which fluids other than blood are involved including gases. For example, plasma exchange filter may be primed using the systems, devices, and methods disclosed. Blood oxygenation filters may also be primed using the systems, devices, and methods disclosed. Filters used for purposes other than blood treatment may also be primed. Also, although the embodiments described generally relate to filters of the type that employ microtubular fiber membranes, the systems, devices, and methods disclosed may be used, or readily adapted for use, with other types of membranes such as pleated membranes, flat membranes, and others. Thus, in embodiments, there is provided, a system in which fluid is contacted with a first side of a membrane while permitting the second side, opposite the first, to remain dry until the fluid contacting the first side traverses the membrane at each point along the membrane. The driving force for fluid progressing along the membrane may be capillary, gravitational, a pumping force, or a combination of these. In embodiments, this is accomplished with, additionally, a mechanism or method that ensures that fluid that completely traverses a first portion of the membrane such that it reaches the second side of the membrane before fluid has traversed a second portion the membrane is prevented from flowing along the second side of the membrane so as to wet the second portion second side of the membrane before said second portion is fully wetted by the traversal of fluid from the second portion first side all the way to the second portion second side. Such mechanisms or methods may include the orientation of the membrane with respect to gravity. Thus, for example, the microtubular fiber type filters discussed above may be oriented with their longitudinal axis in a vertical direction and priming fluid flowed from the bottom such that due to the fluid column, the first portions of the membrane traversed, or more likely to be traversed first, are located at the bottom of the membrane and any fluid collecting on the second side of the membrane remains at the second side bottom due to gravity, which holds fluid collecting on the second side at the lowest part of the second side (in the illustrative embodiments, the non-blood side) compartment.

FIGS. 17A-17F illustrate various devices, methods, and/or systems by which wetting of a first side of a membrane can be done in a manner that helps to ensure that no portions of the second side, opposite the first, are wetted from the second side, to avoid trapping of bubbles within the membrane.

Figure 17A:
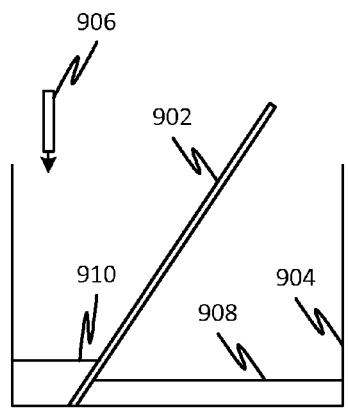
FIGS. 17A-17F illustrate various devices, methods, and/or systems by which wetting of a first side of a membrane can be done in a manner that helps to ensure that no portions of the second side, opposite the first, are wetted from the second side.

Referring to FIG. 17A, a portion of a filter chamber 904 is divided by a membrane 902 and priming fluid flows from a source 906 accumulating a first volume of priming fluid 910 on a first side of the membrane 902. Because of the orientation of the membrane, the first volume of priming fluid 910 collects and is urged by gravity and, possible capillary forces, to traverse the membrane 902 to the second side where a second volume of priming fluid 908 accumulates. Gravity ensures none of the fluid in the second volume can contact the membrane 902 second side until wetted by the volume 910 on the first side as the volume 910 and 908 levels rise due to filling and the transmembrane pressure at the bottom first side is higher than the transmembrane pressure at the top first side. Together, these help to ensure, assuming uniform membrane properties across an area thereof, that the membrane is wetted from the first side to the second side without being first wetted on the second side at any points of the second side surface thereof.

Figure 17B:
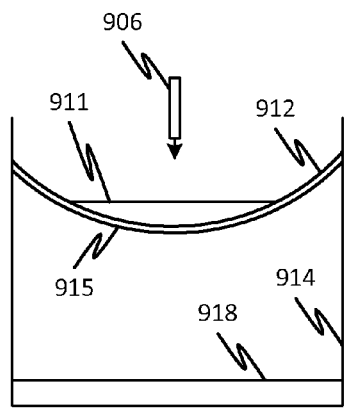

Referring to FIG. 17B, in a portion of a filter chamber 914, priming fluid flows from a source 906 into a lowest point of a curved membrane 912 first side accumulating in a volume 911 on a first side thereof. Fluid can run along the second side and drip to accumulate as volume 918. The shape and orientation of the membrane 912 is such that gravity ensures fluid must flow uphill on the membrane to prematurely wet the second side 915 whilst gravity also ensures, due to the fluid weight column effect, that the fluid is urged more at the lowest point of the membrane than the highest. Together, these help to ensure, assuming uniform membrane properties across an area thereof, that the membrane is wetted from the first side to the second side without being first wetted on the second side at any points of the second side surface thereof.

Figure 17C:
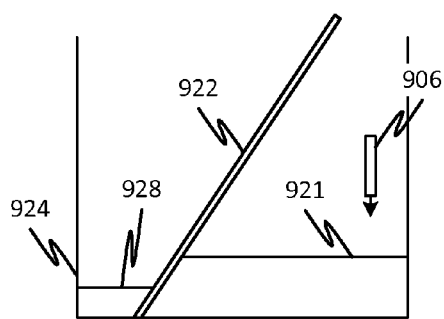

Referring to FIG. 17C, a portion of a filter chamber 924 is divided by a membrane 922 and priming fluid flows from a source 906 accumulating a first volume of priming fluid 921 on a first side of the membrane 922. Because of the orientation of the membrane, the first volume of priming fluid 921 collects and is urged by gravity and, possible capillary forces, to traverse the membrane 922 to the second side where a second volume of priming fluid 928 accumulates. Gravity ensures none of the fluid in the second volume 928 can contact the membrane 922 second side until wetted by the volume 921 on the first side as the volume 921 and 928 levels rise due to filling. The transmembrane pressure at the bottom first side is higher than the transmembrane pressure at the top first side. Together, these help to ensure, assuming uniform membrane properties across an area thereof, that the membrane is wetted from the first side to the second side without being first wetted on the second side at any points of the second side surface thereof.

Figure 17D:
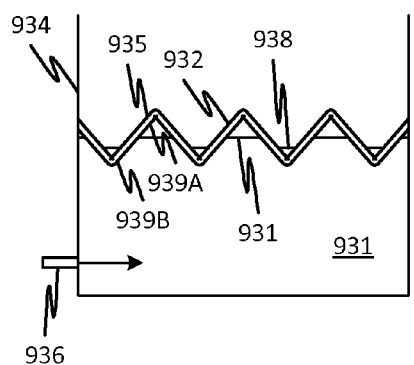

Referring to FIG. 17D, a portion of a filter chamber 934 is divided by a pleated membrane 932 and priming fluid flows from a source 936 accumulating a first volume of priming fluid 931 on a first side of the membrane 932. Because of the arrangement of the membrane, the first volume of priming fluid 931 collects and is urged by gravity and, possible capillary forces, to traverse the membrane 932 to the second side 935 where a second volume of priming fluid 938 accumulates. Gravity ensures none of the fluid in the second volume 938 can contact the membrane 932 second side 935 until wetted by the volume 931 on the first side as the volume 931 and 938 levels rise due to filling. The transmembrane pressure at the lower parts 939B of the first side are higher than the transmembrane pressure at the upper parts 939A of the first side. Together, these help to ensure, assuming uniform membrane properties across an area thereof, that the membrane is wetted from the first side to the second side without being first wetted on the second side at any points of the second side surface thereof.

Forces other than gravity can play a role in ensuring that the membrane is wetted from the first side to the second side without being first wetted on the second side at any points of the second side surface thereof.

Figure 17E:
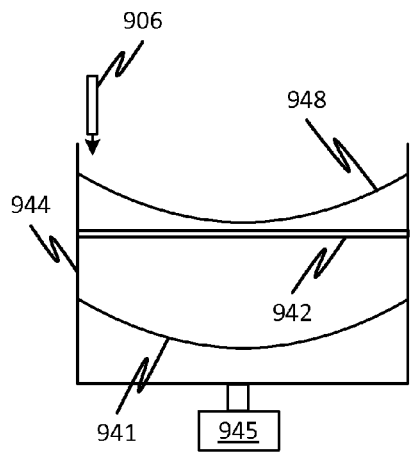

Referring to FIG. 17E, a membrane 942 is held in a rotating filter chamber portion 944. A volume of priming fluid 948 from a source 906 accumulates on a first side of the membrane 942 and is urged in a radially outward direction due to the rotation, which may be caused by a motor 945, for example. Any priming fluid traversing the membrane 942 tends to traverse the membrane first at points furthest out from the center of rotation and any fluid forming on the second side of the membrane will not run along a surface toward the center of rotation but be induced outwardly, thereby helping to avoid prematurely wetting the parts of the membrane 942 second side before they are wetted from flow traversing the membrane 942.

Figure 17F:
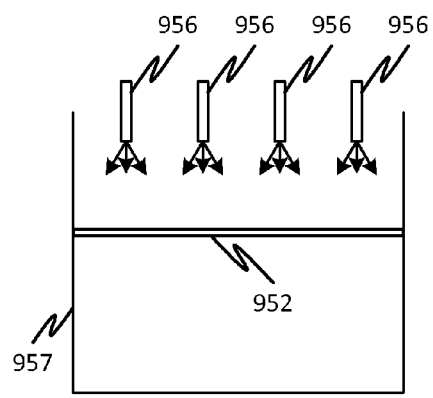

Referring to FIG. 17F, a membrane 952 is supported in a filter chamber portion 957. by spraying from spray heads 956 to uniformly wet a membrane 952 and by limiting the volume of priming fluid such that an amount of fluid is sprayed that is just sufficient to wet the membrane thoroughly, capillary forces may allow the membrane to be fully wetted from a single side. In further embodiments, the volume of priming fluid sprayed may be limited to ensure that no excess, or a limited excess, of priming fluid may accumulate on the membrane 952 second side at any points of the membrane 952 second side so that any such excess cannot flow far or, at least, cannot run to a portion which may not have been fully wetted from the first side.

In all of the embodiments described, the rate of flow of priming fluid may be regulated to help to ensure, in cooperation with the other features described, that a membrane is wetted by flowing from the first side to the second without wetting any portions beforehand from the second side.

Referring now to FIG. 2A, a vent cap 201 which may be used with any of the foregoing and below embodiments includes a cap portion 204 that can be attached and removed by a user from a port, for example, one used to connect non-blood compartment lines to a filter. In embodiments, the cap 201 may be configured to seal and interferingly engage with a predefined port of a predefined filter. In examples, the predefined connector may be a Hansen type port. The vent cap 201 may be used for example at 99, 101, 105, and 148 in the above embodiments. The cap portion 204 has an opening 208 that is covered by a membrane 202 which may be a hydrophobic membrane that is effective to block the flow of water or aqueous solutions through the opening 208 but permit the passage of air. The cap portion 204 may be connectable by threading, a snap fit, or any other suitable mechanism to form a seal. The cap portion 204 may be adapted for fitting to a luer type connector used for making connections to a treatment fluid (i.e., non-blood compartment) system. FIG. 2B shows a priming kit 229 with one or more vented port caps 201 and a container of priming fluid 231. The priming kit may be packaged in a sterile package such a sealed sterile bag.

An alternative to vent cap 201 is to provide a filter with one or more non-blood compartment ports that are covered by hydrophobic membranes which may be punched out by a user after priming is completed. Instead of hydrophobic membranes, such ports may incorporate any of the features described herein including those described in FIGS. 1L through 1P. Other alternatives are ones in which the filter incorporates such venting features in a port separate from the one used for flowing non-blood fluid. The punching out may be caused by the overflow of fluid. Another alternative to the vent cap 201 is a cap with a mechanical valve that block the flow of liquid but permits gas to flow out, for example, a float vent valve (as described with reference to feature 186 of FIG. 1N).

Figure 3:
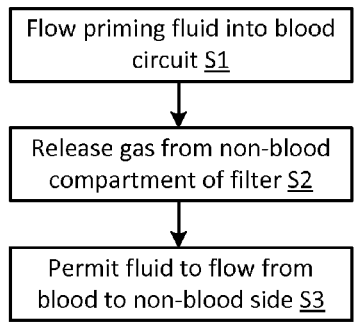
FIG. 3 describes a method of priming, according to embodiments of the disclosed subject matter.

Referring to FIG. 3, as already discussed, priming fluid flows into a blood circuit S1 and contemporaneously the priming fluid causes air to flow through the one or more vents S2 on the non-blood compartment of the filter causing air to be removed from the filter, initially from a blood compartment and then, by flowing through the filter membrane, from the non-blood compartment of the filter S3.

Figure 5:
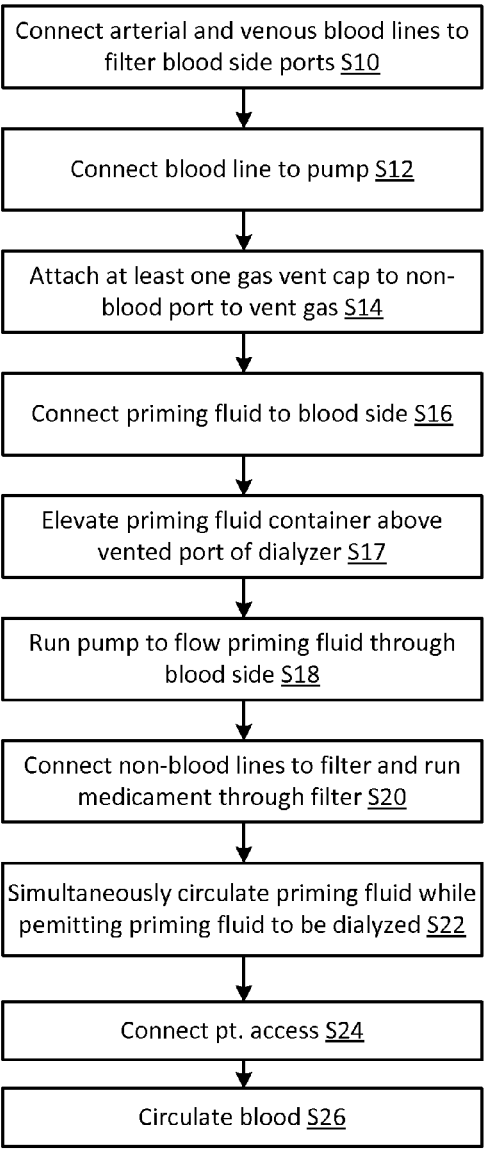
FIG. 5 describes a method of priming, according to embodiments of the disclosed subject matter.

Referring to FIG. 5, in a further method, arterial and venous blood lines are connected to respective filter ports S10. Contemporaneously, blood line pump portion is connected to a pump S12. If not already installed, one or more vents are attached to the filter non-blood compartment ports S14. Priming fluid is connected to the blood compartment according to the configuration S16. The latter step may be effective to form a flow loop, but an additional step may be required of connecting the venous and arterial lines together. The priming fluid container may be elevated above the filter non-blood port(s) so that gravity assists in air removal S17.

The pump may be run to flow the priming fluid through the blood compartment S18. At this point, the operator may have fully connected the blood circuit to a treatment machine, including mounting the filter, so that no further connections, other than connecting the venous and arterial lines to the patient access, are required. Completed priming may be confirmed by visual inspection, a predefined time interval (which may be provided along with instructions for use of the vent system disclosed) or by removing the vent(s) and confirming the presence of fluid at the port(s). The non-blood system may be connected, for example dialysate supply and sink lines may be connected, to the non-blood compartment port(s) S20. If dialysate is connected, the dialysate and priming fluid may be circulated S22 for a predefined interval to cause the priming fluid to dialyze therewith and thereby become essentially the same constitution as the medicament, prior to connecting to the patient which is done at S24. Then treatment may be performed including circulating blood S26.

Figure 4:
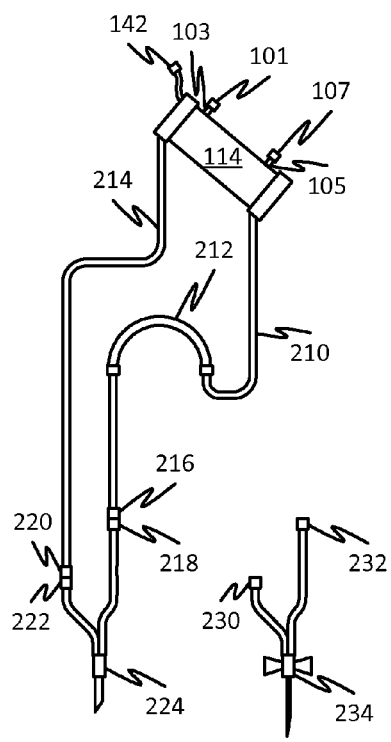
FIG. 4 shows a blood circuit tubing set, according to embodiments of the disclosed subject matter.

FIG. 4 shows a fluid circuit, components, or an entirety, of which may form a deliverable product. A venous line 210 and arterial line 214 are connected to the blood compartment of a filter 114. The filter 114 has ports 103 and 105 with port 103 orientable to a top position relative to the filter. The filter 114 may have an air release port 142 in communication with the blood compartment, for example a blood outlet header of a microtubular fiber membrane bundle type filter. The filter 114 may have, preinstalled thereof or packaged separately and included therewith or with other components, vent caps 101 and 107. Alternative vents or means for allowing gas to exit the non-blood compartment may be provided as discussed with regard to other embodiments. One of the arterial 104 and venous 102 lines may include a pump segment 212. Connectors 216, 218, 220, and 222 may be provided respectively on a dual lumen spike 224 and the venous 102 and arterial 104 lines to permit connection to a container of priming fluid. Alternative connections to a priming fluid container, including separate connections by each of the venous 102 and arterial 104 lines may also be provided for. A patient access 234 with connectors 230 and 232 for connecting respectively to connectors 216 and 220 may also be provided.

In any of the embodiments disclosed, the vented cap 101 may take the form of vent cap 201 of FIG. 2. In any of the embodiments, a fluid circuit may be provided which has a blood circuit and a non-blood circuit portion interconnected by a filter with a blood compartment of the filter being in flow communication with the blood circuit and a non-blood compartment of the filter being in flow communication with the non-blood circuit. Where a fluid circuit is discussed herein, it may be, or include, a blood circuit or have a portion that is a blood circuit portion. In any and all embodiments, the identification as a blood circuit or blood circuit portion or blood compartment provides a reference point and not necessarily the fluid that flows through the respective part. During priming the blood circuit or blood circuit portion of a fluid circuit conveys priming fluid. The fluid circuit may include a filter which may also have blood compartment and non-blood compartments, the former forming part of the blood circuit or blood circuit portion of a fluid circuit. In any of the embodiments, air may be replaced by any gas, for example if a filter were stored with a gas other than air. In any of the embodiments, rather than priming the blood compartment of a fluid circuit by pumping the priming fluid through the circuit, the blood compartment can be configured as a flow loop as discussed, but with the pump not engaged so that gravity may be used to push the priming fluid from the priming fluid container (or other source) into both the blood inlet and outlet ports of the filter. Then air may be removed through the vents on the non-blood ports by gravity without pumping. In any of the embodiments that refer to air, the reference may be replaced by a reference to any gas.

In any of the embodiments, the blood circuit or blood circuit portion may supplied with a non-blood circuit portion in a kit together with other components. For example, the following kits may be provided:

1. A package with one or two vent caps such as vent cap 201.
2. Kit 1, above, with instructions for priming using the vent cap(s) as described according to any of the embodiments herein.
3. One or two vent caps with one or both of an arterial and venous line.
4. One or two vent caps with an arterial and venous line attached by a dual lumen spike.
5. One or two vent caps with an arterial and venous line and a dual lumen spike.
6. One or two vent caps with a filter.
7. One or two vent caps on a filter which is attached to blood lines in a loop closed by a sealed dual lumen spike in the general configuration of FIG. 1B or FIG. 4 thereby forming a hermetically sealed unit with the ports capped or isolated by a membrane that forms a sterile barrier.
8. Any of the above with instructions for priming using the vent cap(s) as described according to any of the embodiments herein.
9. Any of the above kits with a patient access device such as a needle.
10. FIG. 4 with the one or two vent caps pre-installed on non-blood compartment ports of the filter.
11. Any of the kits 1 through 8 with a container of priming fluid.
12. The kit of 9 above where the container has connectors configured for connection to a predefined blood circuit access connectors.
13. Any of the kits 1 through 10 that include a filter, where the filter has a gas release mechanism for the blood compartment, such as air release channel 109 shown in FIG. 6.

Figure 6:
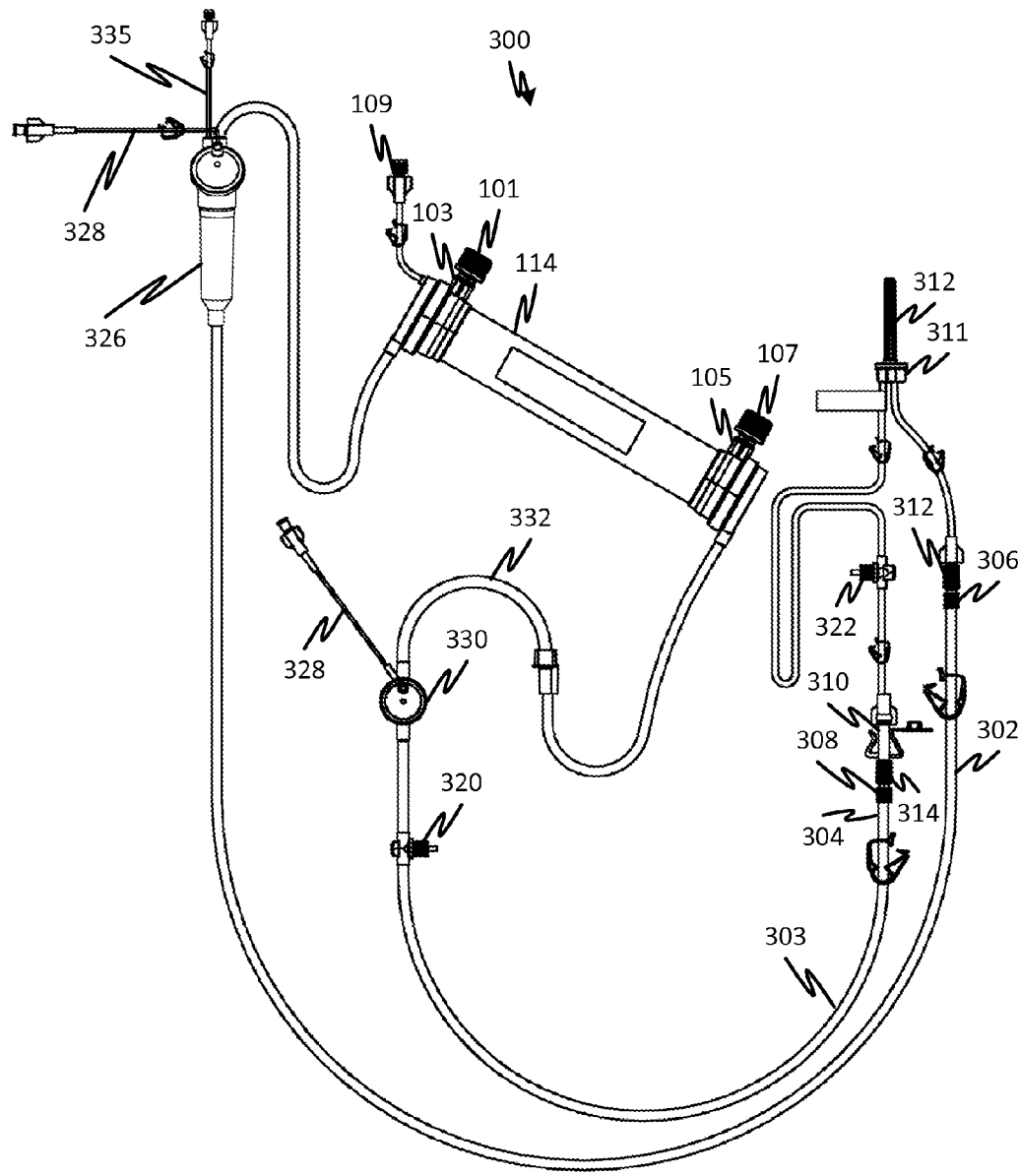
FIG. 6 shows a tubing set, according to embodiments of the disclosed subject matter.

Referring to FIG. 6, a blood circuit 300 has preconnected blood circuit components that, with connector caps in place, form a completely sealed closed loop. The circuit 300 may be completely devoid of fluid, in embodiments. The blood circuit 300, includes a filter 114. The blood circuit 300 components include a pressure measurement pod/air detector 326 (described further with regard to FIG. 7) with a clamped air release line 335, a pressure measurement pod 330, needleless connectors 320 and 322, venous 302 and arterial 303 lines, a pump tubing segment 332, and a filter 114. Filter 114, which may be any of a variety of different types including dialyzer, hemofilter, etc., has an air relief channel 109 which allows air to be removed from an outlet one of the blood compartment headers of the filter 114 during treatment or at other times. Vented caps 101 and 107 on respective ports 103 and 105 are attached to, and seal, the ports 103 and 105. In alternative embodiments, only one vented cap 101 is provided and the other port 105 is sealed by a cap. Arterial 308 and venous 306 access connectors are coupled by coupling elements 310 and 312 to a dual lumen spike 311. The dual lumen spike 311 has a cover 312 which seals the lumens. Air lines 328 are provided on the pressure measurement portions of pressure measurement pod/air detector 326 and pressure measurement pod 330 to convey pressure signals to transducers. The pressure measurement portions of pressure measurement pod/air detector 326 and pressure measurement pod 330 have diaphragms that separate an air chamber from a flow chamber through which blood flows in order to maintain an airless environment for blood flowing therethrough. The air chamber is in communication with the air line 328 in each of the pressure measurement portions of pressure measurement pod/air detector 326 and pressure measurement pod 330. In a variant of the blood circuit 300, the pressure measurement pod/air detector 326 is replaced with pressure measurement pod 330 or vice versa. That is, in the embodiment 300 of FIG. 6, the pressure measurement pod/air detector 326 may be replaced with an inline pressure pod such as described in U.S. Pat. No. 8,491,518 (for example like the one indicated at 33) to form alternative embodiments. In other variations of the embodiment 300, the dual lumen spike 312 is replaced by a pair of connectors for connection to a container for air removal and/or provision of priming fluid. Elements 335 and 328 are optional. Element 326 with elements 335 and 328 is optional. Element 330 is optional. In embodiments, the filter 114, the vent cap or caps 101 and 107 and air relieve channel 109 are provided with a blood circuit of any description. Optionally, the blood circuit access connections may be interconnected to form a sealed loop. The sealed loop of the latter may be closed by a priming fluid container. The latter may be isolated from the blood circuit by frangible connectors or a kink-type connector.

Referring to FIGS. 1C and 1D, experimental work on priming using the priming above-described priming devices, systems, and methods suggests that by fully wetting the membrane in the manner described, the reduction in trapped air bubbles in the membrane can provide several benefits. One is the membrane efficiency is increased. In dialysis treatment, for example, this leads to greater clearance for a given dialyzer. Experimental results also indicate that the efficiency gains are significant as membrane wetting eliminates more and more of the air from the membrane and that the effect is not merely a simple proportionality relationship. A second benefit that may result is that there is significant potential to reduce the need for anti-coagulant devices during treatment when the membrane has been wetted in the manner herein-described. Since air is believed to increase the risk of clotting, residual bubbles in the membrane can adversely increase the risk of clotting.

As explained above, the effect that has been observed is that permitting the outside of each microtubular fiber to be wetted from both sides before all air is removed causes the air to be trapped as bubbles in the pores of the membranes so that the trapped air is not pushed out by the pumping of priming fluid into the lumens of the microtubular fibers. During the described priming processes, priming fluid flows from a blood inlet 147 at an inlet end 145 to a blood outlet 148 at the outlet end 146. As such, priming fluid may be distributed across the header of the inlet end 145 so that all microtubular fiber lumens begin to receive priming fluid at approximately the same time whereafter the priming fluid is forced through the lumens and weeps through the membranes of the microtubular fibers. In a horizontal position as indicated in FIG. 1E, priming fluid may weep to the outside of microtubular fibers positioned at a higher side 191 of the filter 114 and flow onto the outsides of microtubular fibers positioned at a lower side 192 of the filter 114. This may cause the air to be trapped in the microtubular fibers positioned at a lower side 192 of the filter 114. This problem may be mitigated in various ways, at least:

(1) In embodiments of the disclosed subject matter, the orientation of the filter 114 is at least partially vertical as shown in FIGS. 1C and 1D so that priming fluid flows from the bottom, reducing the risk of fluid reaching the outside of microtubular fibers at a higher elevation before fluid weeps to the outside of microtubular fibers at a lower elevation. In more specific embodiments, the filter's longitudinal axis is positioned such that it forms an angle from vertical that is limited to no more than 45 degrees and in further embodiments it is limited to no more than 30 degrees and in still further embodiments to no more than 20 degrees.

(2) In embodiments of the disclosed subject matter, priming fluid may be pumped into the filter 114 at a rate that ensures that the fluid is not forced immediately into higher-elevated microtubular fibers such that it can weep from the higher-elevated microtubular fibers to wet the outsides of lower-elevated microtubular fibers before they are wetted from the inside. Referring to FIG. 1J, a profile 194 figuratively represents variations in the rate at which fluid flows through the microtubular fiber bundle by a profile 194 at where the fluid has reached the outside of the microtubular fibers. At a point 177, fluid seeps from one or more local microtubular fibers and drips or flows to a lower point as indicated by arrow 195 before lower microtubular fibers below that point 177 are wetted from the lumens of the lower microtubular fibers. Note that there may be little inter-tubule coherence so there may not be a smooth profile but this is a figurative illustration. Referring to FIG. 1K, by lowering the flow rate of priming fluid sufficiently, the effect of gravity may be sufficient to ensure the lower microtubular fibers are filled and weep before the upper ones as suggested by the slanted profile 196. In the illustrated embodiments, the force driving fluid into the lower microtubular fibers is significantly influenced by gravity and not dominated by variability in flow resistance such that leading portions of the lower microtubular fibers are more reliably filled before the leading portions of the higher ones. As a result the rate is such that higher priming fluid cannot wet the outside of lower microtubular fibers before such outsides are wetted from the insides.

(3) A filter chamber can be evacuated of air to a very low pressure and filled with priming fluid. If the mass of air is very low as a result of the vacuum, the priming fluid may come from either side of the membrane, and potentially even both, while still achieving a very low amount of air in the fully wetted membrane. In embodiments, the priming fluid can be provided with very low dissolved gases such that the priming fluid is able to absorb residual air in the membrane to further reduce the amount in the membrane once fully wetted. Dissolved gases can be removed by heating the fluid and then isolating from any gases while cooling. The fluid can then be stored in gas-impermeable container such as gas impermeable resin, metalized plastic, metal or composite materials, etc.

In the above discussion, the preferred direction of priming was described as being from the blood to the non-blood side of the membrane. The reason for this is that in the traditional microtubular fiber membranes, if priming fluid is forced inwardly from the outside of the membrane, by attempting to flow priming fluid from the outside of the fibers first, it is more likely that a flow of priming fluid will be generated within the microtubular fibers when fluid weeps into some portions, which flow will reach other portions which have yet to be wetted, thereby trapping air. But if the flow is sufficiently slow, which can be ascertained by experiment for each type of filter, and the orientation is such that gravity plays a significant role such that the fibers are wetted progressively from their lowest ends to the top ends, then the premature wetting caused by flow from a wet portion of the fiber to a dry portion can be minimized. Thus, the embodiments can include microtubular fiber filters in which priming of the blood side is achieved by flowing priming fluid from the outside of the microtubular fibers at a rate and with such transmembrane pressure (a low transmembrane pressure) that the flow within the fiber lumens does not progress any faster than the rate of rise of the wetting of the membrane.

Figure 7:
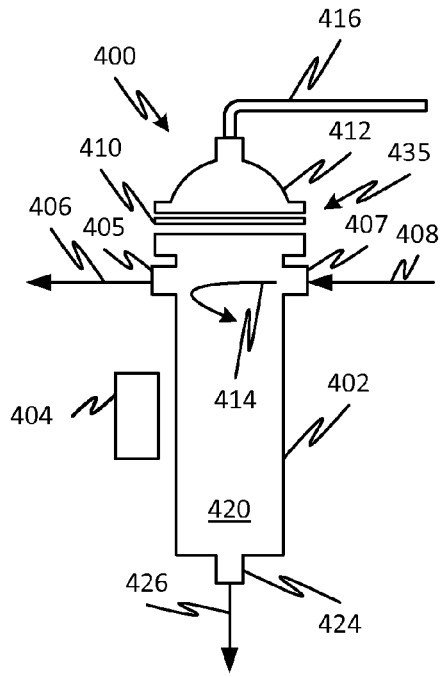
FIG. 7 shows a schematic of a pressure measurement device and an air detector, according to embodiments of the disclosed subject matter.

Referring to FIG. 7, an embodiment of the pressure measurement pod/air detector 326 is illustrated schematically by pressure measurement pod/air detector 400. The air line 416 conveys pressure signals to a transducer. The chamber 412 encloses an air chamber separated by a diaphragm 410 from an internal volume 420 of a blood chamber 402. Flow from the filter 114 flows in a respective port 407 as indicated at 408 and out a respective port 424 as indicated at 426. Air accumulating in the chamber can be released, if necessary, through port 405 as indicated at 406. This may be accomplished by opening a valve on an attached line, such as a pinch clamp. The chamber 420 may be cylindrical and the port 407 may be configured to enter at a tangent to the chamber 420 such that it swirls therein (as indicated by arrow 414), which may help to reduce stagnant regions on the chamber internal volume 420. Although shown exploded at 435, chamber 412, diaphragm 410, and blood chamber 402 are connected so that the chambers are sealed and the diaphragm 410 is trapped and sealed between them. In this way, any change in pressure in the blood flowing in the chamber 402 volume 420 will be reliably transmitted through the diaphragm to the air trapped in chamber 412 and conveyed via the air line 416 to a transducer that may be provided on a blood treatment machine or other device.

Figure 9:
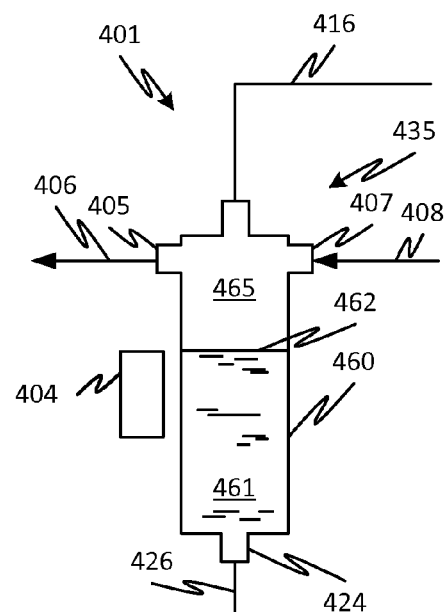
FIG. 9 shows an air pressure measurement device, according to the prior art.

The pressure measurement pod/air detector 400 may be used to replace pressure measurement and air detector units of some legacy systems which are illustrated by the pressure measurement unit 401 (FIG. 9). In prior art pressure measurement devices, the blood 462 is in direct contact with the air that transmits pressure to the transducer. This creates an undesirable risk of thrombogenesis, which pressure measurement pods employing diaphragms can overcome. The prior art device is configured to fit into a detector 404 (or co-located support). The detector 404 is a fluid level detector. The detector 404 indicates when the blood level falls below a predetermined level and the blood treatment machine to which it is connected generates an alarm. An operator may operate a valve to release air from the port 405 and restart the machine.

The embodiment 400 (and 326) are adapted to replace the prior art device 401. Thus, the configuration of the chamber 402 may be selected to fit into the holder of a predetermined prior art blood treatment machine. The chamber 402 may be configured such that the detector 404 is able to detect a fluid level in the chamber volume 420 and thereby appropriately generate an alarm if needed. In the blood circuit 300 of FIG. 6, the function of trapping air is provided by the filter 114 with an air relief channel 109. The details of the filter and air release channel may be as described in U.S. Pat. No. 7,901,579, which is hereby incorporated by reference herein in its entirety. But prior art systems may not function without a device such as 401, 400, 326 being present due to the detector 404 needing to detect fluid in a respective chamber. In other words, the detector 404 may indicate to the prior art blood treatment machine that too much air is present or a safety component may indicate the blood circuit is not fully installed and the machine will not be operable therefore. So the pressure measurement pod/air detector 326, 400 effectively mimics the prior art device 401 so that prior art blood treatment machines can operate.

Pressure measurement pod/air detector 326 and pressure measurement pod 330 may be filled completely with blood. This is possible because there is no need for an air interface because there is a diaphragm. This is desirable because air interfaces can produce problems with clotting.

As described, a blood circuit has an air removal device followed by a blood chamber device with a blood chamber into which blood flows from the air removal device which chamber device is attachable to a blood level detector configured to alarm when a fluid level falls below a predefined level. The chamber device has a diaphragm separating the blood chamber from an air chamber. Air in the air chamber conveys pressure to a transducer. The blood chamber is completely filled with blood during operation of a blood treatment machine. The chamber device serves as a back-up to an existing air removal device in an attached blood circuit. For example, the air removal device may be in an attached filter that forms part of the blood circuit. The filled chamber device indicates to a level detector an acceptable status of the attached blood circuit. The chamber device is delivered as part of a blood circuit that is formed in a closed loop or can be formed as such. The chamber device has an air release.

Figures 10A, 10B:
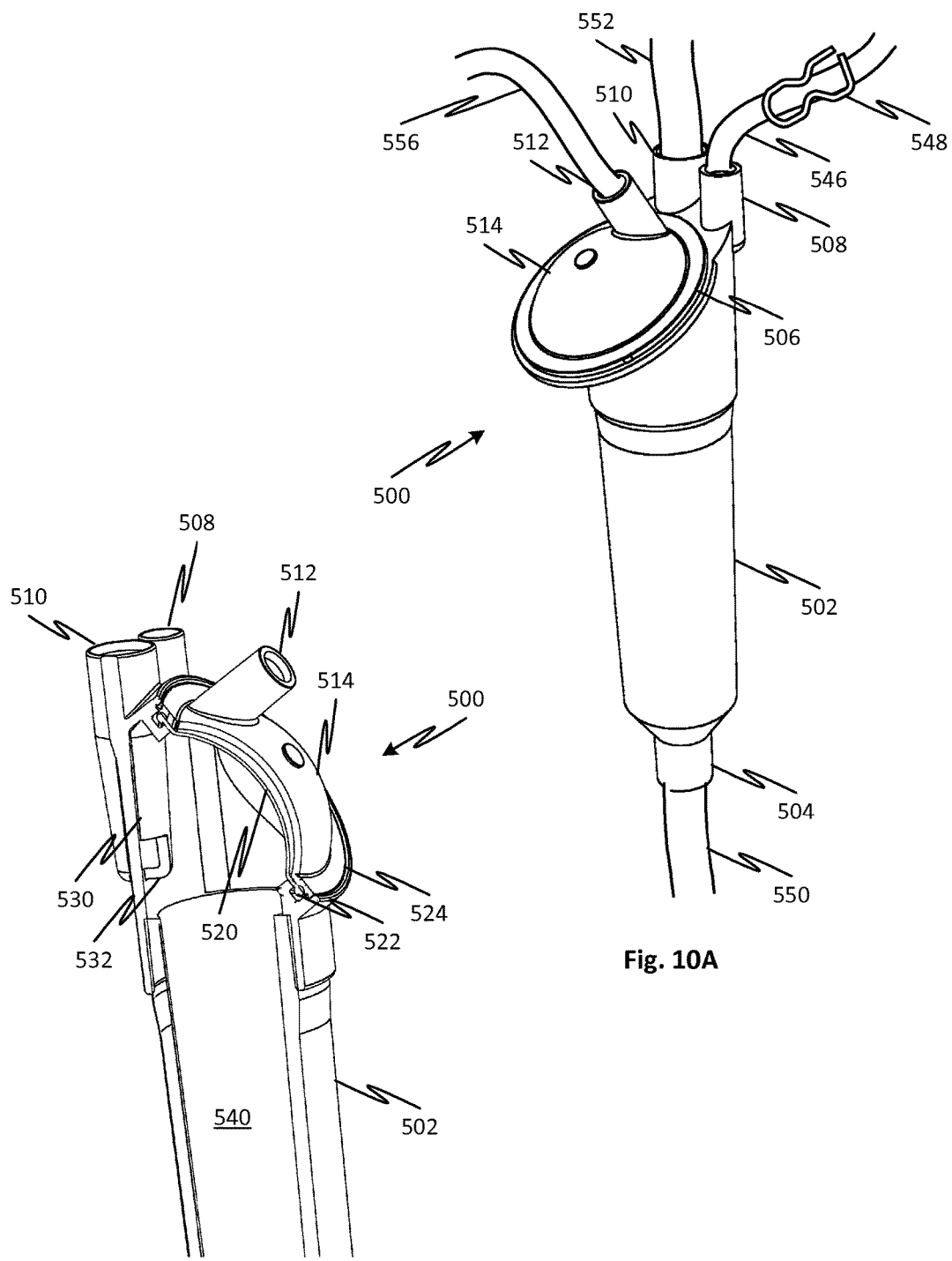
FIGS. 10A and 10B shows a pressure measurement device and an air detector, according to embodiments of the disclosed subject matter.

Referring to FIG. 10A, an embodiment of the pressure measurement pod/air detector 326 is illustrated by pressure measurement pod/air detector 500, which is generically conforms to the major features of pressure measurement pod/air detector 400. An air line port 512 is attachable to an air line (such as air line 416 described above) to convey pressure signals to a transducer. A chamber cover 514 encloses an air chamber separated by a diaphragm 520 from an internal volume 540 of a blood chamber 502. Blood flows in a port 510 and out through port 504. Any air accumulating in the chamber can be released, if necessary, through port 508. This may be accomplished by opening a valve (such as formed using a pinch clamp 548) on an attached line 546, such as a pinch clamp. The chamber 502 may be cylindrical and the port 510 may be configured to enter at a tangent to the internal volume 540. In an embodiment such a tangential entry can be formed by providing a descending plenum 530 that opens on its side (see opening 532) at a position where the internal volume 540 is cylindrical thereby ensuring the tangential flow will generate a persistent swirl effect. A rim 524 of the chamber cover seals with a mating rim 522 of the blood chamber 502 forming an angle with respect to a longitudinal axis of the blood chamber 502. The tangential opening 532 is positioned approximately at the bottom of this rim where the cross-section of the internal volume is at least approximately circular. This allows the swirl generated thereby to persist and keep the blood volume moving therethrough mobile throughout the chamber with minimal eddies that increase the likelihood of clotting.

The diaphragm 520 is sealed around the rim 524 so that any pressure inside the internal volume is transferred to the air space enclosed by the chamber cover and transmitted pneumatically to the port 512. In this way, any change in pressure in the blood flowing in the chamber internal volume 540 will be reliably transmitted through the diaphragm to the air trapped in chamber 514 and conveyed to a transducer that may be provided on a blood treatment machine or other device. The port 508 is in communication with a release line which may be clamped, e.g., by clamp 548. In use, the entire internal volume 540 is filled with blood, which is permitted to contact the diaphragm 520 on one side thereof. If any air accumulates at all, it can be released through the port 508 by, for example, unclamping a line attached thereto. When the blood reaches the line, which may be confirmed by inspection, assuming the line is transparent, the line may be clamped again. This may be done while blood is flowing through the internal volume 540.

The device 500 is configured to replace a predefined unit conforming to the description of prior art device 401. In the device 401, the blood 461 is maintained at an intermediate level 462 inside a chamber 460. The slow movement of blood through the chamber 460 permits air to settle out and collect in the chamber 460. As more air collects, a trapped air volume 465 grows pushing the level 462 down. If the level 462 drops below a certain point, a presence of air (rather than blood) is detected by the sensor 404. An initial quantity of air is provided in the chamber 465 to ensure that air does not reach the air signal line 416. The sensor 404 activates an alarm if the level drops too low to ensure that only blood leaves the outlet 424 and gets to the patient.

In the device 500, the chamber is sized and shaped to fit a level detecting adapter for the chamber 460 of the predefined prior art device 401. The level detector 404 still responds to the presence of air at the detector 404 indicating if level gets too low. This safeguards against air leaving the internal volume 540. If the device 500 is used in place of the prior art device 401, the level sensor 404 can still be used to provide the safeguard against too much air collecting in the chamber. However, in a method of use, an operator release air to ensure that the internal volume 540 is, at all times during a treatment, filled with blood. This eliminates a blood air interface which is beneficial in terms of minimizing clotting in the blood fluid circuit that includes the device 500. The device 500 may be part of a tubing set with blood lines 550 and 552 and air release line 446 and pressure signal line 556 all pre-attached.

Figure 8:
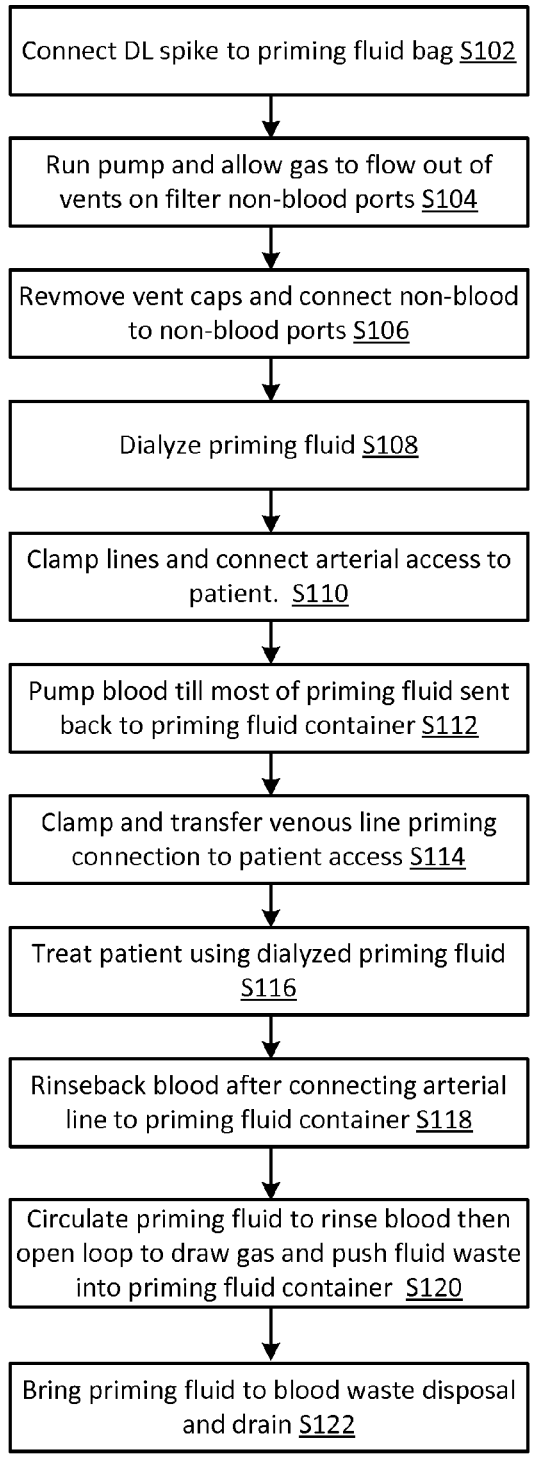
FIG. 8 shows a method of priming, treatment, rinseback, and teardown, according to embodiments of the disclosed subject matter.

Referring to FIG. 8, a method for using the blood circuit 300 and similar embodiments is described. According to a basic embodiment, a closed loop blood circuit is connected to blood treatment machine and a container of saline is attached to the blood circuit venous and arterial connections. No other connections are made to define a fluid flow path such that a sterile flow channel inside the blood circuit is not otherwise opened or previously opened and thereafter connected in order to complete the flow loop. In the method, the flow circuit is fully primed. This has the advantage of avoiding having to make connections that could leak or create contamination. It also has the advantages of avoiding spills and the cumbersome provision of waste containers or sinks to receive priming fluid flowing out of the blood circuit.

A priming fluid container may be provided in the form of a standard 1 L bag. As such the priming fluid may contain compounds from plastic, such as plasticizers, softeners such as BPA, and other elements whose presence is undesirable. After attachment of the dialysate source and sink to ports 103 and 105 of the filter 114, the priming fluid may dialyzed as discussed above. Thus, according to any of the disclosed embodiments, after priming the blood circuit, the entire contents of the priming fluid container may be dialyzed. In embodiments, this includes leaving the priming fluid container in the circuit after priming and dialyzing the contents by continuously recirculating the priming fluid using the dialysate. This may also has the benefit of making the properties of the priming fluid the same as that of the dialysate which has further benefits because patients receive fluid with consistent properties during preparation, treatment, and rinseback. That is, fluid from the container may be delivered to the patient at various times, for flushing the filter via a needle-less port 320, for blood rinseback during patient disconnection, and during initial connection of the patient when a residuum of priming fluid is left in the venous line after connection to the patient access. These desirable properties, particularly the elimination or reduction of potentially toxic materials from the contained priming fluid, are beneficial to patient health and comfort.

In prior art priming, a large amount of priming fluid is disposed of during the priming process as fluid flows, by gravity, through the portions of the circuit. This is because air is purged by providing an opening leading to a waste sink or container and overflow normally occurs. Some method embodiments described herein avoid this waste and thereby conserve priming fluid for use in treatment.

The blood circuit is configured, and a method may provide, that blood waste can be collected in the priming fluid container thereby making it convenient for operators to dispose of the waste in a designated waste disposal sink rather than disposing of a full plastic container and laden fluid circuit as is often done out of convenience according to the prior art. In the method the operator performs rinseback of blood to the patient and rinses the blood lines by reconnecting the venous line and circulating priming fluid through the blood circuit in a closed loop as described with respect to priming. Then the arterial line is opened to the atmosphere and air is pumped through the circuit to push bloody fluid into the priming fluid container. The priming fluid container may then be brought, conveniently, to a liquid waste disposal facility such as a sink and emptied. The result is an empty container, such that the now empty container enters the waste stream rather than a full one (along with a filled blood circuit).

Referring to FIG. 8, at S102, a dual lumen spike is connected to a priming fluid container. In S104, air is vented through vents on the one or more non-blood ports of the filter. In S106, the upper vent cap 101 is removed and the blue dialysate hoses are connected to the non-blood port 103. Then the corresponding is done for the lower non-blood connector 105 and vent cap 107.

In S108, the priming fluid is dialyzed by pumping priming fluid through the priming circuit while dialysate is circulated through the non-blood compartment of the filter 114. In S110, the patient is connected to the arterial access line by clamping the lines and disconnecting the arterial connector (e.g., 308) and connecting it to the patient access. Blood is pumped at S112 until upstream priming fluid is forced back into the container through the dual lumen spike. At S114 the venous line is transferred to the patient access. Then at S116, blood is pumped in the circuit and the patient is treated. At times during treatment, blood may be diluted with fluid from the priming container. As explained above, this blood is modified by dialysis to remove toxins that may appear as a result of the priming fluid being stored in a plastic container.

At S118 the arterial line is reconnected to the priming fluid container and priming fluid (dialyzed priming fluid) is used to rinse blood back into the patient. Then priming fluid may be circulated in the closed loop after reconnecting the arterial line to the priming fluid container to dilute any blood remaining in the circuit. Then at S120 air may be pumped through the loop circuit including the filter by disconnecting the arterial line and running the blood pump. This results in predominantly all the waste fluid ending up in the priming fluid container which may be conveniently dumped at S122 because it is essentially all in a single container which can be emptied easily.

Although the embodiment 300 forms a complete blood circuit whose components are interconnected to form a loop, the components can also be delivered separately and interconnected by the various connectors to form the same product.

Figure 11A:
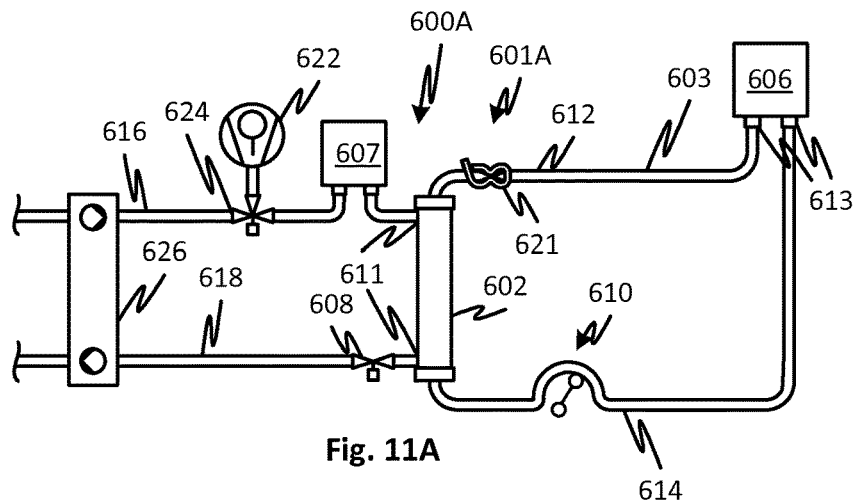
FIG. 11A shows a blood circuit priming configuration employing a vacuum source, according to embodiments of the disclosed subject matter.

Referring to FIG. 11A, a fluid circuit 601A for an extracorporeal blood processing system 600A has a filter 602 that links a blood circuit 603 with a fluid circuit 616, which may be for dialysate. Note that although the embodiments identify dialysate, it should be clear that any kind of medicament may be used, or no medicament at all, as in a hemofiltration system, where the non-blood circuit is used to withdraw waste fluid. So in the present disclosure, any of the embodiments mentioning dialysate or dialysate components may employ other medicaments or no medicaments at all.

The blood circuit includes arterial blood lines 612 and venous blood line 614 joined by a blood compartment of the filter 602 (the lumens of microtubular fiber membranes in the filter 602). The filter 602 may be, as illustrated, a well-known type that has a longitudinal chamber with microtubular fiber membranes held in a bundle therein through which blood flow during a treatment. The filter 602 may have two ports 611 or more (e.g., for hemodiafiltration) for circulating dialysate through the chamber (dialysate compartment). Traditionally, the filter 602 may be oriented vertically with blood pumped upwardly by a blood pump 610 and dialysate pumped downwardly (relative to the filter 602) by a balancing pump 626 in the counter-flow arrangement.

A priming fluid container 606 is attached to the patient connection ports 613 of the arterial and venous blood lines 612 and 614 for a priming process. The priming fluid container 606 as provided may be pre-filled with a sterile priming fluid and connected using a sterile procedure to the patient connection ports 613. The priming fluid, such as blood normal saline, may be pumped through, and circulated in, the blood circuit 603 whilst the priming fluid container serves as an air trap or air settling vessel. That is, the priming fluid container by allowing priming fluid to be circulated therethrough, may permit gas, such as air, to settle out of the recirculating priming fluid. Thus any gas liberated from the filter 602 will be trapped in the priming fluid container 606 during a priming operation in which priming fluid is circulated so at to generate a positive transmembrane pressure (TMP) across the filter membrane, positive being with respect to the direction going from blood compartment to dialysate compartment such that fluid is urged from the blood compartment to the dialysate compartment. The positive TMP may be generated by means of a vacuum pump 622 that is selectively connectable with a dialysate supply line 616.

A dialysate circuit 605 is connected to the filter 602 and includes fresh dialysate supply line 616 and spent dialysate line 618. Dialysate is supplied and drawn off in a balanced fashion by a flow balancing fluid pump 626. A three way control valve 624 selectively connects the dialysate supply line 616 to the filter 602 or a vacuum pump 622 to the filter 602. A control valve 608 may be provided to allows the dialysate return line 618 to be selectively closed during priming so that the vacuum applied by vacuum pump 622 generates a negative pressure in the dialysate compartment. In embodiments, the balancing pump 626 may be configured to close the return line 618 so that a negative pressure is applied to the dialysate compartment of filter 602. For example, a stationary rotor of a peristaltic pump may block any flow thereby closing the return line 618.

A gas and fluid trap 607 may be provided to capture fluid and gas drawn by the negative pressure generated by the vacuum pump 622. In embodiments, the gas and fluid trap 607 and the lines are configured to withstand a low pressure, for example, 0.03 to 0.04 bar, so that a majority of gas can be removed from the filter 602, including the membrane, before allowing priming fluid to flow thereinto. For example, the blood return line 612 can be clamped as indicated by the closed clamp 601. The fluid circuit subjected to negative pressure may be configured generally to handle a strong negative pressure, but not necessarily. According to embodiments, the negative pressure may be approximately, but slightly higher than, the temperature at which an aqueous priming solution will boil at the temperature of priming. The purpose of a very low pressure is to ensure that gas is removed from the filter membrane and other hard-to-clear parts of the filter rather than having to be displaced by the flow of priming fluid, which may be less effective.

Figure 11B:
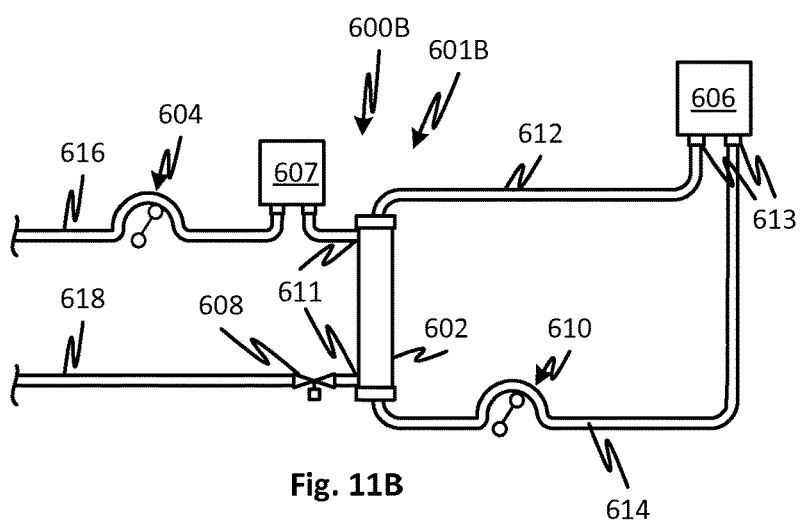
FIG. 11B shows a blood circuit priming configuration employing an auxiliary dialysate circuit pump, according to embodiments of the disclosed subject matter.

FIG. 11B shows a blood circuit priming configuration employing an auxiliary dialysate circuit pump according to embodiments of the disclosed subject matter. An extracorporeal blood processing system 600B has a fluid circuit 601B. The embodiment of FIG. 11B is similar in structure to that of FIG. 11A, with like parts being labeled accordingly. In the blood processing system 600A, an auxiliary dialysate pump 604, such as a peristaltic pump, is provided which may be in place of, or in addition to, a balancing pump such as indicated at 626. The function of the auxiliary dialysate pump 604 is to draw fluid a negative pressure from the filter 602 dialysate compartment. During priming, the blood pump 610 may be run in a forward direction and the auxiliary dialysate pump 604 in a direction so as to draw any liquid or gas out the dialysate compartment and help maintain it under positive TMP (blood to dialysate direction across the membrane) to capture any gas in the gas and fluid trap 607 (which may function to capture gas only, assuming fluid is handled by the dialysate supply line 616). The dialysate supply line 616 may be left disconnected at the end remote from the filter 602 for priming operation. The control valve 608 may seal a lower dialysate port 611 of the filter 602 to support the desired TMP.

In any of the disclosed embodiments, control valves may be automated or manual.

Figure 11C:
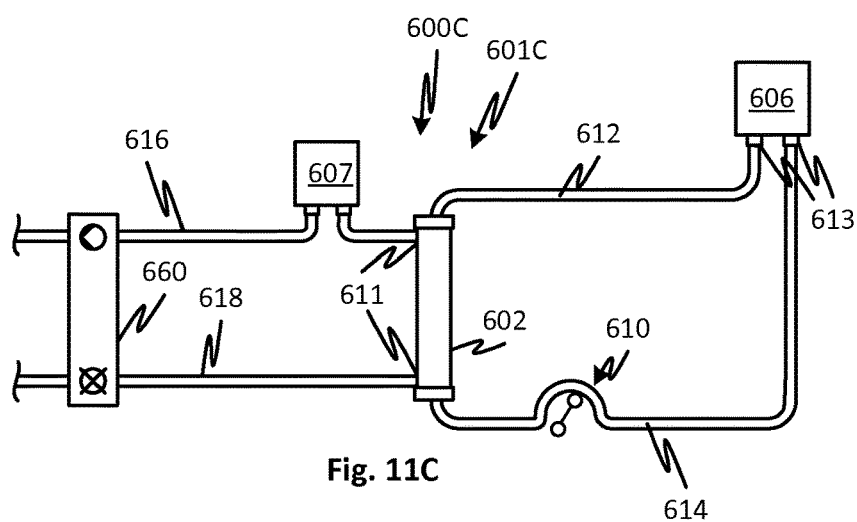
FIG. 11C shows a blood circuit priming configuration employing a reversible balancing pump, according to embodiments of the disclosed subject matter.

FIG. 11C shows a blood circuit priming configuration employing a reversible balancing pump according to embodiments of the disclosed subject matter. An extracorporeal blood processing system 600C has a fluid circuit 601C. The embodiment of FIG. 11C is similar in structure to that of FIGS. 11A and 11B, with like parts being labeled accordingly. Here, the operation is similar to that of the system 600B where a balancing pump 660 is operable in a mode whereby flow in the dialysate return line 618 is stopped to hold the line under the same negative pressure as the dialysate compartment of the filter 602 during priming, and the dialysate supply line is subjected to a negative pressure by a reverse pumping action of the balancing pump 660. In balancing pumps that employ electronic synchronization for flow balancing, this functionality may be provided by a suitable control. For example, in a system with electronically synchronized peristaltic pumps or diaphragm pumps, the dialysate supply line 616 may be pumped in reverse while holding a no-flow condition in the dialysate return line 618, with line closing or clamping as provided.

Figure 12A:
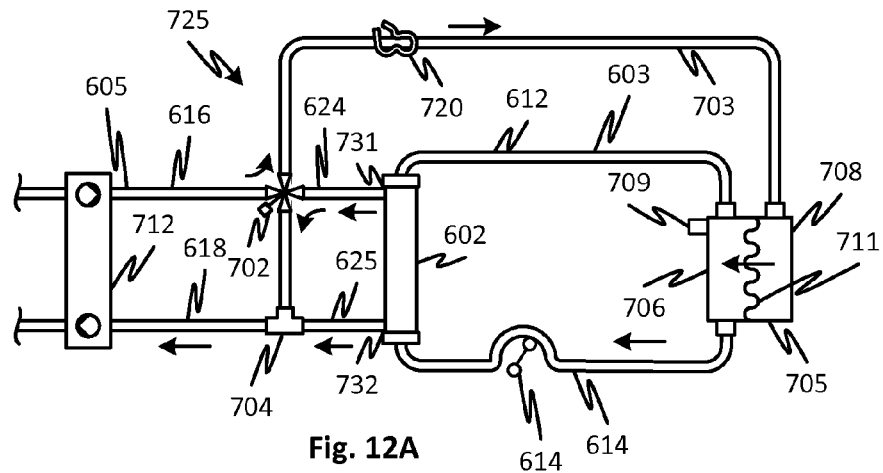
FIG. 12A shows a blood circuit priming configuration employing a dialysate supply for priming and using flow control elements to provide blood circuit priming, according to embodiments of the disclosed subject matter.
Figure 12B:
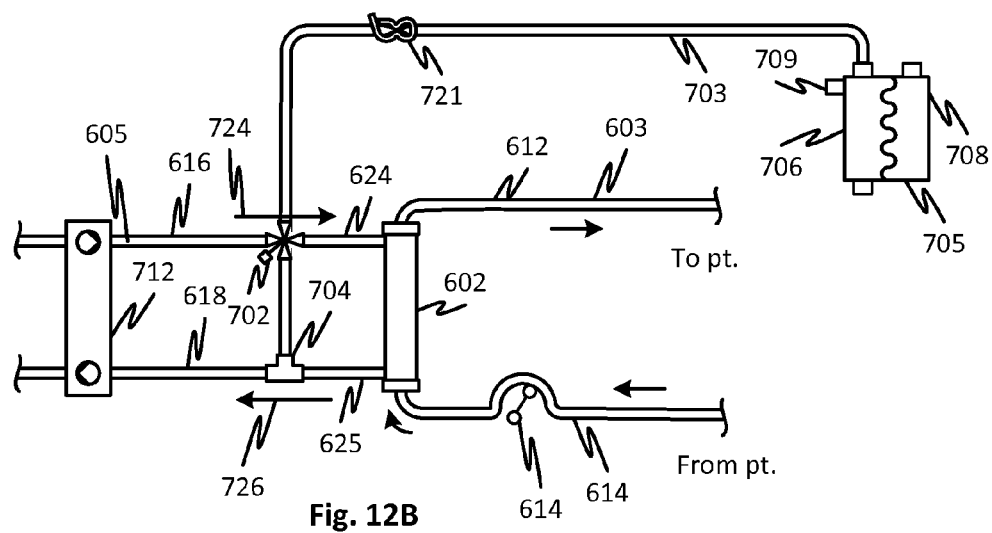
FIG. 12B shows the system of FIG. 12A set up for treatment, according to embodiments of the disclosed subject matter.

FIG. 12A shows a blood circuit priming configuration employing a dialysate supply for priming and using flow control elements to provide blood circuit priming according to embodiments of the disclosed subject matter. A balancing pump 712 supplies dialysate through supply 616 and return 618 lines. A control valve 702 selectively diverts flow as indicated by arrows to provide for a priming path as shown in FIG. 12A and a treatment path as shown in FIG. 12B and discussed below. Further dialysate lines 624 and 625 allow dialysate fluid to be exchanged with the rest of a dialysate circuit 725. A branch line 703 allows dialysate to be pumped into a filtrate compartment 708 of a sterile filter/gas removal chamber 705. A filtrate compartment 706 has a gas relief port 709 which may allow air to be withdrawn or vented automatically according to any of the devices described herein, including, a hydrophobic vent, a septum adapted to receive a regular or blunt hypodermic needle, a manual valve such as a tubing portion with a pinch clamp, or any device that allows fluid level to be controlled. A T branch 704 connects dialysate line 625 with dialysate return line 618. A clamp 720 allows the branch line 703 to be clamped closed.

In a priming process, with the set up depicted in FIG. 12A, the control valve 702 is set so as to divert dialysate conveyed by the balancing pump 712 to the branch line 703 so that it passes through a sterile filter membrane 711 of the sterile filter/gas removal chamber 705 and into the blood circuit 603. The blood pump 614 circulates the dialysate fluid in the blood circuit through venous 614 and arterial 612 portions and through the filtrate compartment 706 of the sterile filter/gas removal chamber 705 where gas may settle out. At this time, the transmembrane pressure across the filter 602 is positive from the blood compartment to the dialysate compartment thereby causing fluid to flow into the membrane until the entire membrane is wetted. Any dialysate that flows out of the dialysate compartment can flow into the lines 624 and/or 625. In a filter 602, which may be a dialyzer with a lower port 732 and an upper port 731, flow through the lower port 732 may be sealed off, optionally, so that all gas is removed through the upper port 731. The may be accomplished by clamping the line 625. In other embodiments, gas and/or fluid may flow from both upper and lower ports 731 and 732. The priming process may continue until all the lines are fully filled with fluid and degassed. It will be observed that the filling of the lines and gas removal may be accomplished without continuous interaction of a user with the system. Once the lines are all filled with fluid, the branch line 703 can be clamped by clamp 721 and arterial 612 and venous 614 lines can be disconnected from the sterile filter/gas removal chamber 705 in preparation for a treatment as shown in FIG. 12B. Once the patient is connected, the control valve 702 may be reconfigured as indicated in FIG. 12B and the dialysate balancing pump and blood pump started in which case the flow across the control valve 702 and through the T junction 704 is as indicated by arrows 724 and 726.

In the priming process described with reference to FIG. 12A, the flow may be as would be generated with the balancing pump 712 operating in an ultrafiltration mode. In the ultrafiltration mode, the volume displacement of fluid from the dialysate circuit 725 is greater than that supplied, which basically means that all the fluid supplied may be withdrawn leaving no excess to recirculate in the blood circuit 603. That is, starting with a dry filter 602, the fluid flows through the filter membrane leaving no excess to flow into the arterial line 612. In a mode that may be more suitable for full priming and wetting of the filter 602 membrane, the balancing pump 712 is operated in a bolus mode at least initially, so as to ensure that there is an excess of fluid to flow through, and recirculating in, the blood circuit 603. In a bolus mode, the balancing pump pumps more fluid into the circuit than it pumps out. Later in a priming process, the balancing pump may progressively move more toward an ultrafiltration mode once the blood and dialysate circuits 603 and 605 are filled. A controller may be programmed to regulate the proportioning, in the range of bolus to ultrafiltration modes, according to a time of operation or using feedback, such as a pressure signal.

Figure 13:
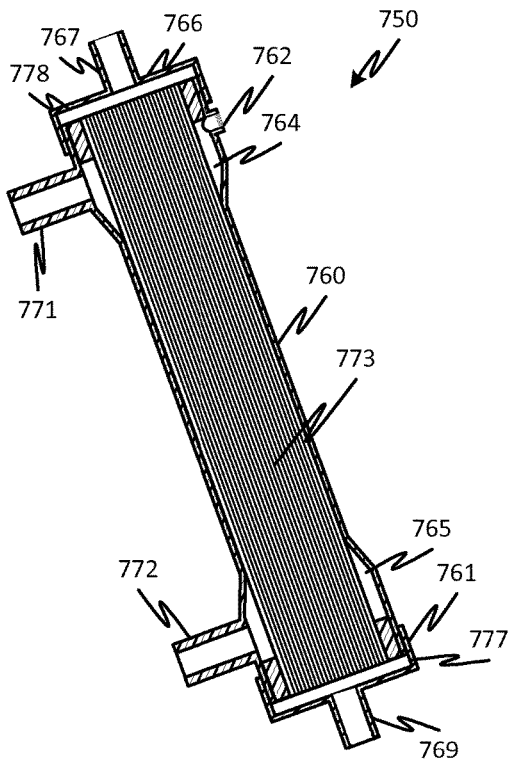
FIG. 13 shows a filter with vent for priming, according to embodiments of the disclosed subject matter.

FIG. 13 shows a filter with vent for priming, according to embodiments of the disclosed subject matter. The filter 750 may be used in the priming configurations of any of FIGS. 1A through 10B because it provides an alternative to the vented caps of the dialysate ports of those embodiments. The filter 750 is of conventional design in most respects comprising a longitudinal dialysate chamber 760 containing a bundle of microtubular fiber membranes 773 that are potted at either end to form an inlet header 777 and an outlet header 778 into which the ends of the microtubular fiber membranes 773 open at respective ends thereof. A dialysate collecting chamber portion 765 receives dialysate from the longitudinal dialysate chamber 760 and conveys the spent dialysate to an outlet port 772. A dialysate distributing chamber portion 764 receives dialysate from the inlet port 771 and conveys the fresh dialysate into the longitudinal dialysate chamber 760. During priming, priming fluid is pumped in the inlet header 777 through the blood inlet port 769 where it flows through the lumens of the microtubular fiber membranes 773 and through the porous microtubular fiber membranes 773 into the longitudinal dialysate chamber 760. A gas-permeable hydrophobic vent 762 allows gas to escape from the longitudinal dialysate chamber 760. In use, the filter 750 may be positioned to place the vent 762 at the highest location of the dialysate distribution chamber portion 764. It will be observed that by locating the vent 762 at a position displaced from the dialysate inlet port 771, the vent may be at a higher elevation relative to the top of the longitudinal dialysate chamber 760 minimizing any volume thereof that could trap gas. The vent may be of a hydrophobic membrane whose pore size is selected to provide a sterile barrier. A cap may be provided in the vent so that it can unsealed during priming and resealed afterward. In embodiments, one or more membrane layers may be provided in the vent 762 which may be spaced apart to prevent growthrough penetration of contaminants.

Figure 14:
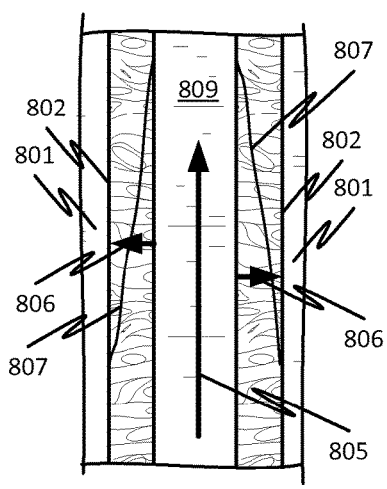
FIG. 14 illustrates the membrane wetting process, according to embodiments of the disclosed subject matter.

FIG. 14 illustrates the membrane wetting process of embodiments of the disclosed subject matter. In embodiments disclosed above and hereafter, a priming fluid is conveyed into a lumen 809 of a microtubular fiber membrane 802 as indicated by arrow 805 so that a TMP (indicated by arrows 806) with respect to the dialysate compartment 801 is generated causing priming fluid to move through the membrane 802. The wet "front" of diffusing priming fluid is indicated figuratively by lines 807. At all time, the membrane 802 remains dry on the dialysate side thereof until it is wetted from the flow from the lumen (blood) side. In this way, gas which is present in the membrane 802 prior to the priming process, is not trapped therein by a fluid front initiated on the dialysate side of the membrane 802. Thus, a one-way flow across the membrane 802 is established at all points of the membrane 802, and this has been found to provide a significant increase in clearance which is believed to result from the unusually low amount of residual air in the membrane 802 after priming.

Figure 15:
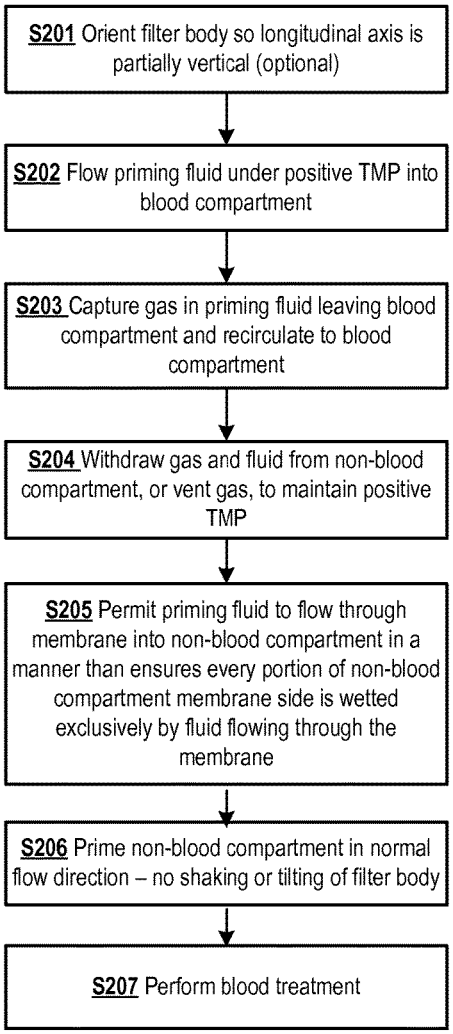
FIG. 15 is a flow chart showing a method for priming a blood circuit and performing a treatment, according to embodiments of the disclosed subject matter.

FIG. 15 is a flow chart showing a method for priming a blood circuit and performing a treatment, according to embodiments of the disclosed subject matter. A filter is oriented in a preferred orientation at S201. In embodiments the preferred orientation may be vertical or it may be slightly tilted as illustrated in the above embodiments. For filter 702, the orientation may include positioning a vent at a highest location or equivalent thereof. At S202, the priming fluid is conveyed to the blood compartment of the membrane and in embodiments, the lumen side of microtubular fiber membranes. In S202 a positive TMP is generated so as to force priming fluid from the lumens outwardly toward the dialysate compartment. In S203, priming fluid may be circulating in the blood circuit and gas recovered from the fluid before returning it to the blood compartment or lumen side of microtubular fiber membranes. In S204, and at least optionally contemporaneously with S203, gas and/or liquid are withdrawn from the dialysate compartment or gas vented therefrom. Alternatively both gas and fluid may be vented from the dialysate compartment. This may help maintain a positive TMP. At S205 and contemporaneously with one or both of S203 and S204, fluid flows through and ultimately thoroughly wets the membrane without fluid entering the dialysate compartment by any other means or otherwise contacting the dialysate side of the membrane until the membrane is fully wetted. At S206, the dialysate compartment may be primed and at S207 a blood treatment may be performed using the primed filter.

Figure 16:
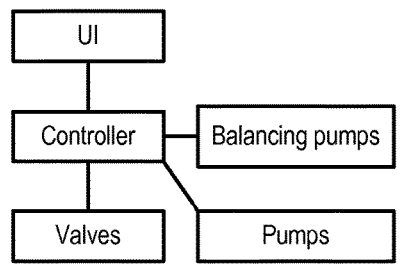
FIG. 16 shows a generalized control system that may be used to control the valves, pumps, and balancing pumps of any of the disclosed embodiments and to convey preprogrammed instructions for performing a priming procedure according to any of the systems or methods described herein.

FIG. 16 shows a generalized control system that may be used to control the valves, pumps, and balancing pumps of any of the disclosed embodiments and to convey preprogrammed instructions for performing a priming procedure according to any of the systems or methods described herein.

In any of the embodiments defined or described herein, the vents that allow gas to exit the filter can be of a configuration that operates as a sterile barrier so that the internal volume of the filter can be isolated against contamination just as if the one or more ports with vents were capped and sealed. In any of the embodiments defined or described herein, the vents that allow gas to exit the filter can be capped to form a sterile barrier so that the internal volume of the filter can be isolated against contamination. Then the cap can be removed to allow the priming operation.

Any of the embodiments employing vented caps may be modified by employing vented plugs, vented adhesive removable seals, or any of the described mechanisms for selectively permitting gas to flow while blocking aqueous fluids.

In any of the embodiments, the fluid described may be replaced by any aqueous fluid or any non-aqueous fluid. In any of the embodiments described, the membrane may of any construction including hydrophilic or hydrophobic components or combinations thereof.

According to first embodiments, the disclosed subject matter includes a method of priming a blood circuit of a blood treatment system of a type whose control of a blood circuit pump thereof permits pumping in a single direction, only. The method includes connecting a blood circuit having a filter and venous and arterial lines to blood treatment machine pump. The method further includes pumping fluid from a source of fluid through the blood circuit and filter while flowing the priming fluid from a blood compartment of the filter through the membrane to a non-blood compartment of the filter.

Any of the first embodiments may be modified, where possible, to form additional first embodiments that include connecting the blood circuit to a source of priming fluid such that the venous and arterial portions are interconnected to form a flow loop. Any of the first embodiments may be modified, where possible, to form additional first embodiments in which the pumping includes pumping fluid continuously through the flow loop. Any of the first embodiments may be modified, where possible, to form additional first embodiments in which the connecting includes connecting access connectors of the arterial and venous lines to the source of fluid, the access connectors being adapted for connecting a patient access to the venous and arterial lines. Any of the first embodiments may be modified, where possible, to form additional first embodiments in which the access connectors are connected to the source of priming fluid. Any of the first embodiments may be modified, where possible, to form additional first embodiments in which the access connectors are connected to the source of priming fluid through a dual lumen connector that connects both the arterial and venous lines to the source of priming fluid. Any of the first embodiments may be modified, where possible, to form additional first embodiments in which the source of priming fluid is a container. Any of the first embodiments may be modified, where possible, to form additional first embodiments that include settling air out of the priming fluid and into the container while flowing the priming fluid continuously through the flow loop. Any of the first embodiments may be modified, where possible, to form additional first embodiments that include venting air from at least one port coupled to the non-blood compartment of the filter. Any of the first embodiments may be modified, where possible, to form additional first embodiments in which venting includes passing air through at least one liquid-blocking vent attached to that at least one port. Any of the first embodiments may be modified, where possible, to form additional first embodiments in which the at least one liquid-blocking vent includes a cap with a hydrophobic membrane. Any of the first embodiments may be modified, where possible, to form additional first embodiments in which the at least one liquid-blocking vent includes a removable cap with a hydrophobic membrane. Any of the first embodiments may be modified, where possible, to form additional first embodiments in which the filter is a dialyzer, the at least one liquid-blocking vent includes a removable cap with a hydrophobic membrane. Any of the first embodiments may be modified, where possible, to form additional first embodiments in which the filter is of the type having a bundle of microtubular fiber membranes with the blood compartment including a parallel circuit that includes the lumens of the membranes. Any of the first embodiments may be modified, where possible, to form additional first embodiments in which the at least one liquid-blocking vent includes a cap with a hydrophobic membrane. Any of the first embodiments may be modified, where possible, to form additional first embodiments in which the at least one liquid-blocking vent includes a removable cap with a hydrophobic membrane. Any of the first embodiments may be modified, where possible, to form additional first embodiments in which the at least one liquid-blocking vent includes a removable cap with a membrane that provides a sterile barrier. Any of the first embodiments may be modified, where possible, to form additional first embodiments in which the filter is a dialyzer, the at least one liquid-blocking vent includes a removable cap with a hydrophobic membrane. Any of the first embodiments may be modified, where possible, to form additional first embodiments that include orienting the filter such that the at least one port is positioned at a highest point of the filter body. Any of the first embodiments may be modified, where possible, to form additional first embodiments in which the filter is positioned with a longitudinal access thereof oriented at a diagonal with the vertical. Any of the first embodiments may be modified, where possible, to form additional first embodiments that include installing the filter in an attachment to hold the filter and leaving it the holder for priming and for a performing a blood treatment without removing the filter or changing its orientation. Any of the first embodiments may be modified, where possible, to form additional first embodiments in which the attachment holds the filter in a fixed position. Any of the first embodiments may be modified, where possible, to form additional first embodiments in which the pumping is at a predetermined volumetric flow rate selected for priming. Any of the first embodiments may be modified, where possible, to form additional first embodiments in which the priming fluid is sterile saline.

A system may be configured to implement any of the foregoing methods. A fluid circuit may be configured to implement any of the foregoing methods.

According to second embodiments, the disclosed subject matter includes a kit for priming a blood treatment circuit. The kit includes at least one cap, having an opening in a central region thereof. The kit further includes a hydrophobic membrane attached to the cap and covering the hole such that water or aqueous fluid is prevented from flowing through the hole but air or other gas is not. The kit further includes a blood circuit portion, a blood treatment filter, or instructions for priming a fluid circuit used for extracorporeal blood treatment.

Any of the second embodiments may be modified, where possible, to form additional second embodiments in which the blood circuit portion, blood treatment filter, or instructions for priming a fluid circuit used for extracorporeal blood treatment includes a blood circuit portion. Any of the second embodiments may be modified, where possible, to form additional second embodiments in which the blood circuit portion, blood treatment filter, or instructions for priming a fluid circuit used for extracorporeal blood treatment instructions for priming a fluid circuit used for extracorporeal blood treatment. Any of the second embodiments may be modified, where possible, to form additional second embodiments in which the blood circuit portion, blood treatment filter, or instructions for priming a fluid circuit used for extracorporeal blood treatment a blood treatment filter. Any of the second embodiments may be modified, where possible, to form additional second embodiments in which the at least one cap includes the two caps identified above.

Any of the second embodiments may be modified, where possible, to form additional second embodiments which include a blood line or a patient access. Any of the second embodiments may be modified, where possible, to form additional second embodiments in which the instructions identify one or more blood treatment machines which have controllers whose control of pumping is limited to starting and stopping the pump and allowing the speed of the pump to be selected by an operator. Any of the second embodiments may be modified, where possible, to form additional second embodiments in which the instructions identify one or more blood treatment machines which have controllers whose control of pumping is limited to functions that do not include reversal of the pump or reversal of the flow in the blood circuit by other means.

According to third embodiments, the disclosed subject matter includes a blood circuit for a blood treatment system with a preconnected loop with arterial and venous blood line connectors connected together by a device for attaching both to a fluid container. The preconnected loop has a pumping portion, a blood treatment filter, and at least one pressure measuring device.

Any of the third embodiments may be modified, where possible, to form additional third embodiments in which the preconnected loop includes tubing and a pumping portion configured to engage with a peristaltic pump. Any of the third embodiments may be modified, where possible, to form additional third embodiments in which the preconnected loop is enclosed in a sterile container. Any of the third embodiments may be modified, where possible, to form additional third embodiments in which an interior volume of the preconnected loop is sealed from the ambient. Any of the third embodiments may be modified, where possible, to form additional third embodiments in which the device for attaching is a dual lumen bag spike. Any of the third embodiments may be modified, where possible, to form additional third embodiments in which the blood treatment filter has one or more non-blood ports, further comprising a cap configured to fit on the one or more non-blood ports, the cap having a hydrophobic air vent. Any of the third embodiments may be modified, where possible, to form additional third embodiments in which the blood treatment filter has one or more non-blood ports with a cap configured on the one or more non-blood ports, the cap having a hydrophobic air vent. Any of the third embodiments may be modified, where possible, to form additional third embodiments that include a first air trap with an air release. Any of the third embodiments may be modified, where possible, to form additional third embodiments that include a second air trap with an air release connected downstream of the first air trap and adapted to engage a fluid level detector.

According to fourth embodiments, the disclosed subject matter includes a method of using a blood circuit for a blood treatment device that include connecting a priming fluid container to a blood circuit. The method further includes priming the circuit after making no more than two fluid connections to a priming fluid container. The method includes emptying fluid and from the circuit into the priming fluid container by pushing with air until the circuit is emptied of fluid and emptying the priming fluid container of its contents into a waste disposal facility at a point of care. Any of the fourth embodiments may be modified, where possible, to form additional fourth embodiments in which emptying fluid and from the circuit is effective to place all fluid in the circuit in the priming fluid container.

According to fifth embodiments, the disclosed subject matter includes a pressure measurement and air detection device for a blood tubing set has an elongate cylindrical chamber with a first internal volume adapted to fit into a predefined bracket configured to detect a fluid level. The first internal volume has an inlet and a bottom outlet, the outlet is at a bottom end thereof and the inlet is located above the outlet. The elongate cylindrical chamber has a top air outlet port that serves as an air outlet in communication with the first internal volume, the top air outlet port has a tube and a clamp arranged to permit the tube to be selectively closed. The first internal volume is closed by a diaphragm attached to the elongate cylindrical chamber at a top end thereof. A top chamber, smaller in size than the elongate cylindrical chamber and located a top thereof, has a second internal volume separated by the diaphragm from the first internal volume such that a pressure of fluid in the first internal volume exerted on the diaphragm presses against air trapped in the second internal volume forcing air out of the top air outlet port.

According to sixth embodiments, the disclosed subject matter includes a method for trapping air in a blood circuit and for measuring pressure without an air interface includes providing an elongate cylindrical chamber with a first internal volume adapted to fit into a predefined bracket configured to detect a fluid level. The first internal volume has an inlet and a bottom outlet, the outlet is at a bottom end thereof and the inlet is located above the outlet. The elongate cylindrical chamber has a top air outlet port that serves as an air outlet in communication with the first internal volume, the top air outlet port has a tube and a clamp arranged to permit the tube to be selectively closed. The first internal volume is closed by a diaphragm attached to the elongate cylindrical chamber at a top end thereof. a top chamber with a pressure signal port, the top chamber is smaller in size than the elongate cylindrical chamber and located at a top of the elongate cylindrical chamber, the top chamber has a second internal volume separated by the diaphragm from the first internal volume such that a pressure of fluid in the first internal volume exerted on the diaphragm presses against air trapped in the second internal volume forcing air out of the pressure signal port. According the sixth embodiment, the method includes connecting the pressure signal port to a pressure sensor. The method further includes filling the entire first internal volume with blood such that a surface of the diaphragm is in contact with the blood, the filling includes flow blood through the inlet and out the outlet. The method further includes unclamping the tube to prevent to release any air from the first internal volume and ensure there is no air interface within the first internal volume. The method further includes during a treatment, releasing any air that accumulates in the first internal volume by unclamping the tube. The method further includes during the treatment, measuring a pressure using the transducer.

According to seventh embodiments, the disclosed subject matter includes, a method for performing a blood treatment includes providing a dry blood filter. The method further includes flowing priming fluid into a blood compartment of the dry blood filter and letting the priming fluid flow from the blood compartment, through the membrane, into the dialysate compartment until the entire membrane is fully wetted exclusively from the flow from the blood compartment, to provide a wet blood filter. The method further includes, after said flowing until the membrane is fully wetted, connecting a source of dialysate to the dialysate compartment of the wet blood filter and performing a blood treatment that includes flowing dialysate through said dialysate compartment and blood through said blood compartment.

Additional seventh embodiments may be formed wherein said letting the priming fluid flow through the membrane includes flowing priming fluid until the entire dialysate compartment is full as a result of said flowing through said membrane before said performing a blood treatment. Additional seventh embodiments may be formed wherein the flowing is such that the dialysate compartment fills progressively from one longitudinal end to the other. Additional embodiments may be formed by configuring apparatus to perform any of the foregoing method claims.

According to embodiments, the disclosed subject matter includes a control system configured to convey instructions to a user for performing the methods of any of the seventy embodiments.

According to eighth embodiments, the disclosed subject matter includes blood treatment device with a medicament compartment and a blood compartment separated by a treatment membrane. The medicament compartment has a gas vent formed therein at a top-most position of the medicament compartment, the gas vent has hydrophobic membrane that is effective as a sterile barrier.

The eighth embodiments can be modified to form further eighth embodiments in which the device of the vent may have two spaced apart sterile barrier membranes. In eight embodiments can be modified to form further eighth embodiments in which the treatment membrane is a bundle of microtubular membrane fibers. In eight embodiments can be modified to form further eighth embodiments in which the vent is remotely from a port in communication with the medicament compartment. In eight embodiments can be modified to form further eighth embodiments that include instructions for implementing the method of using the device. In eight embodiments can be modified to form further eighth embodiments that include instructions for using the device of FIG. 16 to implement the method of FIG. 15.

According to ninth embodiments, the disclosed subject matter includes a method of using a porous membrane having pores and first and second sides separated by a thickness of the membrane. The method includes flowing fluid through the membrane from the first side so as to ensure that each portion of the second side area of the membrane is wetted exclusively by flow through a corresponding portion of the first side which is directly opposite the each portion of the second side area, such that fluid is prevented from reaching said each portion of the second side area from the second side before is fully wetted by flow from said corresponding portion of the first side, whereby gas is displaced through the membrane without is trapped by fluid flowing into the membrane from the second side.

The ninth embodiments can be modified to form additional ninth embodiments wherein the membrane includes hydrophobic and hydrophilic materials. The ninth embodiments can be modified to form additional ninth embodiments wherein the membrane is housed in a dialyzer. The ninth embodiments can be modified to form additional ninth embodiments wherein the flowing fluid through the membrane includes flowing the fluid along the membrane first side while generating a positive transmembrane pressure. The ninth embodiments can be modified to form additional ninth embodiments wherein the flowing fluid through the membrane includes flowing the fluid along the membrane first side while generating a positive transmembrane pressure using a pump. The ninth embodiments can be modified to form additional ninth embodiments, wherein the flowing fluid through the membrane includes flowing the fluid along the membrane first side while generating a positive transmembrane pressure using gravity. The ninth embodiments can be modified to form additional ninth embodiments wherein the flowing fluid through the membrane includes flowing the fluid along the membrane in a direction that is against the pull of gravity. The ninth embodiments can be modified to form additional ninth embodiments wherein the flowing fluid through the membrane includes flowing the fluid along the membrane in a direction that is against the pull of gravity and the local transmembrane pressure at each point of said membrane is significantly caused by the weight of a fluid column whereby the transmembrane pressure progressively decreases in the vertical direction therealong.

According to tenth embodiments, the disclosed subject matter includes a blood circuit kit for a blood treatment system. The kit includes a blood line with at least one connector configured to attach the blood line to a predefined blood treatment filter and a cap has a hydrophobic vent, the cap is configured fit on a port of the same predefined blood treatment filter.

The tenth embodiments can be modified to form additional tenth embodiments that include a dual lumen bag spike. The tenth embodiments can be modified to form additional tenth embodiments wherein the dual lumen bag spike is pre-attached to the blood line. The tenth embodiments can be modified to form additional tenth embodiments wherein the components of the kit are enclosed in a sterile bag. The tenth embodiments can be modified to form additional tenth embodiments wherein the blood line has arterial and venous portions that are interconnected. The tenth embodiments can be modified to form additional tenth embodiments, wherein the blood line has arterial and venous portions that are interconnected by the dual lumen bag spike. The tenth embodiments can be modified to form additional tenth embodiments that include the predefined blood treatment filter. The tenth embodiments can be modified to form additional tenth embodiments wherein the predefined blood treatment filter is preconnected to the blood line and the cap is attached to the predefined connector so as to form a sealed volume that includes a lumen of the blood line and the filter. The tenth embodiments can be modified to form additional tenth embodiments, wherein the cap has a further impermeable cap that covers the hydrophobic vent. The tenth embodiments can be modified to form additional tenth embodiments, wherein the hydrophobic vent includes a hydrophobic membrane that is configured to function as a sterile barrier.

According to eleventh embodiments, the disclosed subject matter includes a blood circuit kit for a blood treatment system that includes a blood line with at least one connector configured to attach the blood line to blood compartment ports of a predefined blood treatment filter. A cap has a hydrophobic vent and is configured fit on a non-blood compartment port of the same predefined blood treatment filter.

The eleventh embodiments can be modified to form additional eleventh embodiments that include a dual lumen bag spike. The eleventh embodiments can be modified to form additional eleventh embodiments, wherein the dual lumen bag spike is preattached to the blood line. The eleventh embodiments can be modified to form additional eleventh embodiments, wherein the components of the kit are enclosed in a sterile bag. The eleventh embodiments can be modified to form additional eleventh embodiments, wherein the blood line has arterial and venous portions that are interconnected. The eleventh embodiments can be modified to form additional eleventh embodiments, wherein the blood line has arterial and venous portions that are interconnected by the dual lumen bag spike. The eleventh embodiments can be modified to form additional eleventh embodiments that include the predefined blood treatment filter. The eleventh embodiments can be modified to form additional eleventh embodiments wherein the predefined blood treatment filter is preconnected to the blood line and the cap is attached to the predefined connector so as to form a sealed volume that includes a lumen of the blood line and the filter. The eleventh embodiments can be modified to form additional eleventh embodiments, wherein the cap has a further impermeable cap that covers the hydrophobic vent. The eleventh embodiments can be modified to form additional eleventh embodiments, wherein the hydrophobic vent includes a hydrophobic membrane that acts as a sterile barrier. The eleventh embodiments can be modified to form additional eleventh embodiments, wherein the predefined filter is a dialyzer. The eleventh embodiments can be modified to form additional eleventh embodiments, wherein the blood compartment is separated from the non-blood compartment by microtubular fiber membranes.

According to twelfth embodiments, the disclosed subject matter includes a device for a blood treatment. In the device, a blood treatment filter has a chamber with a blood compartment and a non-blood compartment and blood ports opening to the blood compartment and at least one non-blood port opening to the non-blood compartment. The blood and non-blood compartments is separated by a filter membrane. A vent is integrated in said chamber has a hydrophobic barrier that is permeable to gas but which blocks aqueous liquids, the vent is positioned to allow gas in said non-blood compartment to flow therethrough to an outside of said chamber.

The twelfth embodiments can be modified to form additional twelfth embodiments that include instructions for priming according to any of the method embodiments. The twelfth embodiments can be modified to form additional twelfth embodiments that include a seal attached to said vent. The twelfth embodiments can be modified to form additional twelfth embodiments wherein the vent includes a hydrophobic membrane configured to block pyrogens. The twelfth embodiments can be modified to form additional twelfth embodiments, wherein the vent includes a hydrophobic membrane with a pore size of no greater than 0.3 micron. The twelfth embodiments can be modified to form additional twelfth embodiments, wherein the at least one non-blood port is positioned opposite said vent on said chamber. The twelfth embodiments can be modified to form additional twelfth embodiments, wherein the blood treatment filter has a longitudinal axis and said vent is positioned at a position along said longitudinal axis that allows the vent to be located at a highest point within the volume of said non-blood compartment.

According to thirteenth embodiments, the disclosed subject matter includes a kit for a blood treatment, the kit including a blood treatment filter has a chamber with a blood compartment and a non-blood compartment and blood ports opening to the blood compartment and at least one non-blood port opening to the non-blood compartment. The blood and non-blood compartments is separated by a filter membrane. A vented cap has a hydrophobic barrier that is permeable to gas but which blocks aqueous liquids, the vented cap is configured to cover and seal non-blood port and configured to allow gas in said non-blood compartment to flow therethrough to an outside of said chamber.

The thirteenth embodiments can be modified to form additional thirteenth embodiments, wherein the vented cap is attached to said at least on non-blood port. The thirteenth embodiments can be modified to form additional thirteenth embodiments that include instructions for priming according to any of the method embodiments. The thirteenth embodiments can be modified to form additional thirteenth embodiments, wherein the vented cap hydrophobic barrier includes a membrane. The thirteenth embodiments can be modified to form additional thirteenth embodiments, wherein the vented cap hydrophobic barrier includes a membrane with a pore size of no more than 0.3 micron. The thirteenth embodiments can be modified to form additional thirteenth embodiments, wherein the vented cap hydrophobic barrier includes a membrane that is effective to form a sterile barrier.

According to fourteenth embodiments, the disclosed subject matter includes a kit for a blood treatment with a blood treatment filter has a chamber with a blood compartment and a non-blood compartment and blood ports opening to the blood compartment and at least one non-blood port opening to the non-blood compartment. The blood and non-blood compartments is separated by a filter membrane. A vented fluid channel has a gas vent with a hydrophobic barrier that is permeable to gas but which blocks aqueous liquids, the fluid channel is configured for attachment to said at least one non-blood port and configured to cover and seal said non-blood port and allow gas in said non-blood compartment to flow therethrough to an outside of said chamber.

The fourteenth embodiments can be modified to form additional fourteenth embodiments, wherein the vented fluid channel is attached to said at least on non-blood port. The fourteenth embodiments can be modified to form additional fourteenth embodiments that further include instructions for priming according to any of the disclosed methods. The fourteenth embodiments can be modified to form additional fourteenth embodiments, wherein the vented fluid channel hydrophobic barrier includes a membrane. The fourteenth embodiments can be modified to form additional fourteenth embodiments, wherein the vented fluid channel hydrophobic barrier includes a membrane with a pore size of no more than 0.3 micron. The fourteenth embodiments can be modified to form additional fourteenth embodiments, wherein the vented fluid channel hydrophobic barrier includes a membrane that is effective to form a sterile barrier.

According to fifteenth embodiments, the disclosed subject matter includes, a method for priming a blood circuit that includes connecting a blood circuit to a container of priming fluid and a filter and pumping priming fluid in a loop through the blood circuit so as to allow said priming fluid to wet a membrane of said filter while allowing said priming fluid to flow into said non-blood compartment by passing through said membrane and allowing gas to escape from a non-blood compartment of said filter while blocking said priming fluid from leaking from said non-blood compartment when it fills said non-blood compartment. A flow rate of said pumping is selected to prevent any priming fluid from passing through said membrane at a first region of the membrane above a second region of the membrane such that said second region can be wetted from a non-blood surface thereof before said second region is fully wetted by flow through said membrane due to flow along said non-blood surface from said first region to said second region.

The allowing gas to escape while blocking may include providing a hydrophobic membrane positioned to vent gas from the non-blood compartment. The allowing gas to escape while blocking may include positioning a device on a non-blood port of the filter that seals with the non-blood port of the filter, the device has a vent that passively vents gas from the non-blood compartment while blocking aqueous fluid. The allowing gas to escape while blocking may include positioning a cap on a non-blood port of the filter that seals with the non-blood port of the filter, the cap has a vent that passively vents gas from the non-blood compartment while blocking aqueous fluid. The vent may include a hydrophobic barrier element. The fifteenth embodiments may be modified to form additional fifteenth embodiments, wherein the vent includes a hydrophobic membrane. The fifteenth embodiments may be modified to form additional fifteenth embodiments, wherein the filter is a dialyzer. The fifteenth embodiments may be modified to form additional fifteenth embodiments, wherein the filter is a device used in renal replacement therapy. The fifteenth embodiments may be modified to form additional fifteenth embodiments that include using the blood circuit to perform a blood treatment.

According to sixteenth embodiments, the disclosed subject matter includes a method for priming a blood circuit including connecting at least a portion of a blood circuit to a container of priming fluid and a blood compartment of a filter and flowing priming fluid through the blood circuit into the blood compartment so as to allow said priming fluid to wet a membrane of said filter while allowing said priming fluid to flow into said non-blood compartment by passing through said membrane and allowing gas to escape from a non-blood compartment of said filter while blocking said priming fluid from leaking from said non-blood compartment when it fills said non-blood compartment. The flowing is induced by gravity such as to prevent any priming fluid from passing through said membrane at a first region of the membrane above a second region of the membrane such that said second region can be wetted from a non-blood surface thereof before said second region is fully wetted by flow through said membrane due to flow along said non-blood surface from said first region to said second region by the establishment of a pressure gradient that progressively decreases with the height of respective regions of the membrane.

The sixteenth embodiments may be modified to form additional sixteenth embodiments, wherein the allowing gas to escape while blocking includes providing a hydrophobic membrane positioned to vent gas from the non-blood compartment. The sixteenth embodiments may be modified to form additional sixteenth embodiments, wherein the allowing gas to escape while blocking includes positioning a device on a non-blood port of the filter that seals with the non-blood port of the filter, the device has a vent that passively vents gas from the non-blood compartment while blocking aqueous fluid. The sixteenth embodiments may be modified to form additional sixteenth embodiments, wherein the allowing gas to escape while blocking includes positioning a cap on a non-blood port of the filter that seals with the non-blood port of the filter, the cap has a vent that passively vents gas from the non-blood compartment while blocking aqueous fluid. The sixteenth embodiments may be modified to form additional sixteenth embodiments, wherein the vent includes a hydrophobic barrier element. The sixteenth embodiments may be modified to form additional sixteenth embodiments, wherein the vent includes a hydrophobic membrane. The sixteenth embodiments may be modified to form additional sixteenth embodiments, wherein the filter is a dialyzer. The sixteenth embodiments may be modified to form additional sixteenth embodiments, wherein the filter is a device used in renal replacement therapy. The sixteenth embodiments may be modified to form additional sixteenth embodiments that include using the blood circuit to perform a blood treatment. The sixteenth embodiments may be modified to form additional sixteenth embodiments that include allowing gas to vent from a blood port of said filter. The sixteenth embodiments may be modified to form additional sixteenth embodiments, wherein the allowing gas to vent from a blood port of said filter includes venting gas from the filter blood compartment as a result of displacement of gas from lumens of microtubular fiber membranes. The sixteenth embodiments may be modified to form additional sixteenth embodiments, wherein the allowing gas to vent from a blood port of said filter includes passing said gas through a hydrophobic barrier. The sixteenth embodiments may be modified to form additional sixteenth embodiments, wherein the allowing gas to vent from a blood port of said filter includes passing said gas through a hydrophobic barrier integrated in a cap sealed to a blood compartment port of said filter. The sixteenth embodiments may be modified to form additional sixteenth embodiments, that include orienting a longitudinal axis of said filter in at least partially vertical direction. The sixteenth embodiments may be modified to form additional sixteenth embodiments that include orienting said filter to place at least one gas vent at a top-most position of said non-blood compartment. The sixteenth embodiments may be modified to form additional sixteenth embodiments, wherein the blocking is performed passively, without action by a user.

According to seventeenth embodiments, the disclosed subject matter includes a method for preparing a blood circuit for a treatment process that includes priming a blood circuit includes a dialyzer using priming fluid from a container, the priming being effective to fill the blood circuit, a blood compartment of the filter, and a dialysate compartment of the filter. The method further includes dialyzing the priming fluid left in the blood circuit for a time sufficient to substantially remove contaminants from said priming fluid before connecting said blood circuit to a patient.

The seventeenth embodiments may be modified to form additional seventeenth embodiments, wherein the dialyzing includes disposing of dialysate after passing it through said dialysate compartment.

According to eighteenth embodiments, the disclosed subject mattes includes a method for rinsing blood back to a patient after an extracorporeal blood treatment. The method includes flowing an infusible fluid in a blood circuit includes a dialyzer, the blood circuit forming a loop includes a container and dialyzing the infusible fluid for a time sufficient to substantially remove contaminants from said priming fluid and storing dialyzed infusible fluid in said container before connecting said blood circuit to a patient. The method further includes using said dialyzed infusible fluid stored by said storing to rinse blood back to a patient following said extracorporeal blood treatment. The eighteenth embodiments may be modified to form additional eighteenth embodiments, wherein the dialyzing includes disposing of dialysate after passing it through said dialysate compartment. The eighteenth embodiments may be modified to form additional eighteenth embodiments, wherein the flowing includes priming the blood circuit using the infusible fluid.

The foregoing descriptions apply, in some cases, to examples generated in a laboratory, but these examples can be extended to production techniques. For example, where quantities and techniques apply to the laboratory examples, they should not be understood as limiting.

It will be appreciated that the modules, processes, systems, and sections described above can be implemented in hardware, hardware programmed by software, software instruction stored on a non-transitory computer readable medium or a combination of the above. For example, a method for priming can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of fluid circuits, pumps, control systems, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, methods, devices, and systems for priming. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method of priming a blood circuit of a blood treatment system of a type whose control of a blood circuit pump thereof permits pumping in a single direction, only, the method comprising:
 connecting a blood circuit that includes
  a filter that includes a bundle of microtubular fiber membranes with lumens of the microtubular fiber membranes fluidly connected to a blood compartment of the filter and the lumens extending through a non-blood compartment of the filter, the non-blood compartment having at least one port,
  venous lines, and
  arterial lines
   to a blood treatment machine pump;
 orienting the filter such that the at least one port is positioned at a highest point of the non-blood compartment of the filter and the at least one port includes a liquid-blocking vent fluidly connected to the non-blood compartment of the filter;
 pumping a priming fluid from a source of the priming fluid through the blood circuit and the filter in a single direction into the blood compartment of the filter;
 flowing the priming fluid from the blood compartment of the filter into the lumens of the microtubular fiber membranes;
 the flowing being such that an exterior surface of the microtubular membranes remains dry until the exterior surface is wetted from the flow of the priming fluid from the lumens through the microtubular fiber membranes to the non-blood compartment of the filter;
 collecting air that is pushed out of the microtubular fiber membranes in the non-blood compartment and
 venting said air through the liquid-blocking vent fluidly connected to the non-blood compartment of the filter.

2. The method of claim 1, further comprising connecting the blood circuit to the source of the priming fluid such that the venous and arterial portions are interconnected to form a flow loop.

3. The method of claim 2, wherein the pumping includes pumping the priming fluid continuously through said flow loop.

4. The method of claim 2, wherein said connecting includes connecting said arterial and venous lines to said source of the priming fluid.

5. The method of claim 4, wherein said connecting the arterial and venous lines includes connecting to said source of the priming fluid through a dual lumen connector that connects both the arterial and venous lines to the source of the priming fluid.

6. The method of claim 5, wherein the source of the priming fluid is a container.

7. The method of claim 1, wherein the at least one liquid-blocking vent includes a cap with a hydrophobic membrane.

8. The method of claim 1, wherein the at least one liquid-blocking vent includes a removable cap with a hydrophobic membrane.

9. The method of claim 1, wherein the filter is a dialyzer, and the at least one liquid-blocking vent includes a removable cap with a hydrophobic membrane.

10. The method of 1, wherein the lumens of the membranes extend in parallel within the filter.

11. The method of claim 10, wherein the at least one liquid-blocking vent includes a cap with a hydrophobic membrane.

12. The method of claim 10, wherein the at least one liquid-blocking vent includes a removable cap with a hydrophobic membrane.

13. The method of claim 10, wherein the at least one liquid-blocking vent includes a removable cap with a membrane that provides a sterile barrier.

14. The method of claim 10, wherein the filter is a dialyzer, the at least one liquid-blocking vent includes a removable cap with a hydrophobic membrane.

15. The method of claim 1, wherein the filter is positioned with a longitudinal access thereof oriented at a diagonal with the vertical.

16. The method of claim 1, further comprising installing the filter in an attachment to hold the filter and leaving it in the attachment for priming and for performing a blood treatment without removing the filter or changing its orientation.

17. The method of claim 16, wherein the attachment holds the filter in a fixed position.

18. The method of claim 1, wherein the pumping is at a predetermined volumetric flow rate selected for priming.

19. The method of claim 1, wherein the priming fluid is sterile saline.

20. The method of claim 18, wherein the predetermined volumetric flow rate is selected to prevent the priming fluid from passing through the microtubular fiber membranes at a first region of the membranes, above a second region of the membranes, before the priming fluid passes through the microtubular fiber membranes at the second region, and the second region is not wetted from the exterior surface thereof before said second region is wetted by the passing of the priming fluid through the microtubular membrane.

\* \* \* \* \*